US012721931B2

(12) United States Patent
Nakai et al.

(10) Patent No.: US 12,721,931 B2
(45) Date of Patent: Sep. 1, 2026

(54) FLEXIBLE TUBE FOR ENDOSCOPE, ENDOSCOPIC MEDICAL DEVICE, AND METHODS FOR PRODUCING THE SAME

(71) Applicant: FUJIFILM Corporation, Tokyo (JP)

(72) Inventors: Yoshihiro Nakai, Ashigarakami-gun (JP); Kazushi Furukawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 673 days.

(21) Appl. No.: 18/147,302

(22) Filed: Dec. 28, 2022

(65) Prior Publication Data

US 2023/0135925 A1 May 4, 2023

Related U.S. Application Data

(63) Continuation of application No. PCT/JP2021/024361, filed on Jun. 28, 2021.

(30) Foreign Application Priority Data

Jun. 29, 2020 (JP) ................................ 2020-111755

(51) Int. Cl.
*A61L 29/06* (2006.01)
*A61L 29/02* (2006.01)

(52) U.S. Cl.
CPC ............... *A61L 29/06* (2013.01); *A61L 29/02* (2013.01)

(58) Field of Classification Search
CPC ........ A61L 29/06; A61L 29/02; A61L 29/085; A61L 29/14; A61B 1/005; B29C 63/06; B32B 1/08; B32B 15/09; C08J 5/12
See application file for complete search history.

(56) References Cited

U.S. PATENT DOCUMENTS

2002/0048678 A1 4/2002 Hunia et al.
2020/0100652 A1 4/2020 Yoshitani et al.

FOREIGN PATENT DOCUMENTS

JP 11-42205 A 2/1999
JP 2004-141487 A 5/2004
JP 2004-242963 A 9/2004
JP 2007-144783 A 6/2007
JP 2008-070900 A 3/2008
(Continued)

OTHER PUBLICATIONS

English machine translation for WO2019013243. (Year: 2019).*
(Continued)

*Primary Examiner* — Michael C Miggins
(74) *Attorney, Agent, or Firm* — Sughrue Mion, PLLC

(57) ABSTRACT

Provided are a flexible tube for an endoscope, the flexible tube having a flexible-tube base containing metal as a constituent material, a cover layer covering an outer periphery of the flexible-tube base, and a primer layer disposed between the flexible-tube base and the cover layer and including at least one of a specific silane coupling agent, an aluminum alkoxide compound, a zirconium alkoxide compound, or a titanium alkoxide compound, in which the cover layer includes, at least on a side in contact with the primer layer, a polyester having a naphthalene structure, an endoscopic medical device using the flexible tube, a method for producing the flexible tube for an endoscope, and a method for producing the endoscopic medical device.

18 Claims, 2 Drawing Sheets

(56) References Cited

FOREIGN PATENT DOCUMENTS

| | | | |
|---|---|---|---|
| JP | 2008-308511 | A | 12/2008 |
| WO | 2019/013243 | A1 | 1/2019 |

OTHER PUBLICATIONS

International Search Report dated Sep. 14, 2021 in Application No. PCT/JP2021/024361.

Written Opinion of the International Searching Authority dated Sep. 14, 2021 in Application No. PCT/JP2021/024361.

International Preliminary Report on Patentability dated Dec. 13, 2022 with a Translation of the Written Opinion of the International Searching Authority in Application No. PCT/JP2021/024361.

Japanese Office Action dated Oct. 3, 2023 in Application No. 2022-533995.

* cited by examiner

FLEXIBLE TUBE FOR ENDOSCOPE, ENDOSCOPIC MEDICAL DEVICE, AND METHODS FOR PRODUCING THE SAME

CROSS-REFERENCE TO RELATED APPLICATIONS

This application is a Continuation of PCT International Application No. PCT/JP2021/024361 filed on Jun. 28, 2021, which claims priority under 35 U.S.C. § 119 (a) to Japanese Patent Application No. 2020-111755 filed in Japan on Jun. 29, 2020. Each of the above applications is hereby expressly incorporated by reference, in its entirety, into the present application.

BACKGROUND OF THE INVENTION

1. Field of the Invention

The present invention relates to a flexible tube for an endoscope, an endoscopic medical device, and methods for producing the same.

2. Description of the Related Art

Endoscopes are medical devices for examining the inside of the body cavity, the inside of the digestive tract, the esophagus, or the like of a patient. Since endoscopes are inserted and used in the body, it is desirable to provide endoscopes that do not damage organs or cause pain or discomfort to a patient. In view of such a requirement, a spiral tube formed by spirally winding a soft, bendable metal strip is adopted as a flexible tube that forms an insertion section of an endoscope. Furthermore, the periphery of the spiral tube is covered with a flexible resin so that the spiral tube does not cause stimulation, damage, or the like to the inner surface of, for example, the esophagus, digestive tract, or body cavity.

Endoscopes for examining the inside of the human body are repeatedly used. In order to allow an endoscope insertion section to reach an affected part or the like smoothly and reliably, the endoscope insertion section is repeatedly bent. Therefore, the endoscope insertion section is required to have a characteristic (bending durability) that a flexible-tube base and a cover layer for this flexible-tube base are unlikely to peel off even when the insertion section is repeatedly bent.

As a technology for addressing this problem, JP1999-42205A (JP-H11-42205A) discloses a flexible tube for an endoscope, the flexible tube including a flexible-tube base material formed by fitting a mesh tube into an outer periphery of a spiral tube, and an outer cover covering an outer periphery of the flexible-tube base material and formed of a thermoplastic elastomer, in which the flexible-tube base material and the outer cover are formed so as to be in close contact with each other via a coupling agent such as a silane-based, titanate-based, aluminum-based, or zirconium-based coupling agent having a function of adhering to both an inorganic substance and an organic substance. WO2019/013243A discloses a flexible tube for an endoscope, the flexible tube having a flexible-tube base containing metal as a constituent material and a resin cover layer covering an outer periphery of the flexible-tube base, in which the flexible tube has, between the flexible-tube base and the resin cover layer, a primer layer including a specific silane compound, and the resin cover layer includes a polyurethane elastomer at least on a side in contact with the primer layer, so that the resin cover layer is less likely to peel off from the flexible-tube base.

In addition, the flexible tube that forms the insertion section of an endoscope needs to be washed and disinfected with a chemical each time it is used. In particular, when the flexible tube is inserted into a highly susceptible region, such as the bronchus, cleanliness at a level of sterilization higher than disinfection is required. Accordingly, a flexible tube for an endoscope is required to have high durability enough to withstand repeated sterilization treatment.

With regard to cleaning durability of a flexible tube, for example, JP2004-141487A describes a flexible tube for an endoscope, the flexible tube being formed by covering a surface of a flexible-tube base material with an outer cover, in which polybutylene naphthalate is used as a hard segment of a polyester elastomer constituting the outer cover, and discloses that, with this configuration, degradation of the outer cover due to a washing solution or a disinfecting solution can be suppressed, and durability to sterilization treatment using an autoclave can also be improved.

SUMMARY OF THE INVENTION

The improvement of adhesiveness between a flexible-tube base and a cover layer thereof is an important requirement in durability of endoscope products, and further improvement of the adhesiveness is required.

In addition, with regard to sterilization durability of a flexible tube for an endoscope, in recent years, chemical sterilization treatment using hydrogen peroxide plasma, ethylene oxide gas, or the like has also been widely performed instead of autoclave treatment from the viewpoint of suppressing hygrothermal aging of the flexible tube for an endoscope. Furthermore, recently, sterilization treatment using ozone water in which a very small amount of ozone ($O_3$) is dissolved in water has been performed. This ozone water produces strong active species such as hydroxy radicals, and the oxidizing power thereof is stronger than that of hydrogen peroxide gas. Accordingly, substantially only fluororesins are known as organic materials that can withstand the sterilization treatment with ozone water.

In view of the above points, an object of the present invention is to provide a flexible tube for an endoscope, the flexible tube being capable of sufficiently maintaining adhesiveness between a flexible-tube base and a cover layer covering the flexible-tube base even when a bending movement is repeated and being unlikely to be subjected to a decrease in adhesiveness between the flexible-tube base and the cover layer even when subjected to strong sterilization treatment with ozone water, and an endoscopic medical device using the flexible tube. Another object of the present invention is to provide a method for producing the flexible tube for an endoscope and a method for producing the endoscopic medical device.

As a result of extensive studies in view of the problems described above, the inventors of the present invention have found that the above problems can be solved by using a polyester having a naphthalene structure incorporated therein as a constituent material of a cover layer (outer cover) that forms a flexible tube for an endoscope, and in the preparation of the flexible tube for an endoscope, providing, on an outer periphery of a flexible-tube base, a primer layer including at least one of an aluminum alkoxide compound, a zirconium alkoxide compound, a titanium alkoxide compound, or a specific silane coupling agent, and providing the cover layer with the primer layer between the flexible-tube base and the cover layer. This finding has led to the completion of the present invention.

The above objects have been achieved by the following means.

<1>

A flexible tube for an endoscope, the flexible tube having a flexible-tube base containing metal as a constituent material; a cover layer covering an outer periphery of the flexible-tube base; and a primer layer disposed between the flexible-tube base and the cover layer and including at least one of a silane coupling agent, an aluminum alkoxide compound, a zirconium alkoxide compound, or a titanium alkoxide compound, wherein the cover layer includes, at least on a side in contact with the primer layer, a polyester having a naphthalene structure.

However, the silane coupling agent includes none of a vinyl silane coupling agent, a (meth)acrylic silane coupling agent, an epoxy silane coupling agent, an amino silane coupling agent, and a sulfanyl silane coupling agent.

<2>

The flexible tube for an endoscope according to <1>, wherein the silane coupling agent includes a compound represented by general formula (1) below.

General formula (1)

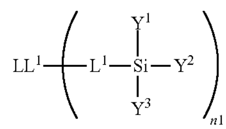

In the formula, $LL^1$ represents a monovalent substituent or an n1-valent linking group. $L^1$ represents a single bond or a divalent linking group. $Y^1$ to $Y^3$ each represent a substituent. n1 is an integer of 1 to 4.

However, at least one of $Y^1$ to $Y^3$ is a group selected from the group consisting of alkoxy groups and a hydroxy group, and when n1 is 1, $LL^1$, $LL^1$-$L^1$, and $Y^1$ to $Y^3$ do not simultaneously represent groups selected from the group consisting of alkoxy groups and a hydroxy group. The compound represented by general formula (1) includes none of a vinyl silane coupling agent, a (meth)acrylic silane coupling agent, an epoxy silane coupling agent, an amino silane coupling agent, and a sulfanyl silane coupling agent.

<3>

The flexible tube for an endoscope according to <2>, wherein the compound represented by general formula (1) includes a compound represented by any of general formulae (2) to (4) below.

General formula (2)

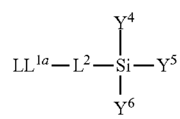

General formula (3)

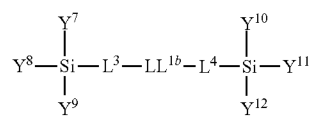

-continued

General formula (4)

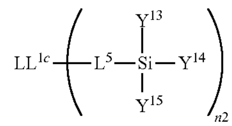

In the formulae, $LL^{1a}$ represents a hydrogen atom, an alicyclic group, a heterocyclic group, a hydroxy group, a sulfanyl group, an isocyanato group, a thiocyanato group, a ureido group, a cyano group, an acid anhydride group, an azide group, a carboxy group, an acyl group, a thiocarbamoyl group, a phosphoric acid group, a phosphanyl group, a sulfonic acid group, or a sulfamoyl group.

$L^2$ represents a single bond, an alkylene group, an alkenylene group, an alkynylene group, an arylene group, —O—, —S—, —$NR^a$—, an ester bond, a thioester bond, an amide bond, a thioamide bond, a sulfonyl group, or a divalent group formed by combining two or more selected from the group consisting of the aforementioned groups and bonds.

$L^3$ to $L^5$ each represent a single bond, an alkylene group, an alkenylene group, an alkynylene group, an arylene group, —O—, —S—, —$NR^a$—, an ester bond, a thioester bond, an amide bond, a thioamide bond, a urea bond, a thiourea bond, a sulfonyl group, or a divalent group formed by combining two or more selected from the group consisting of the aforementioned groups and bonds.

$LL^1$represents a single bond, an alkylene group, an alkenylene group, an alkynylene group, an arylene group, —O—, —S—, —$NR^a$—, a divalent heterocyclic group, an amide bond, an ester bond, a thioester bond, a divalent phosphoric acid group, a phosphanediyl group, a sulfonyl group, or a divalent group formed by combining two or more selected from the group consisting of the aforementioned groups and bonds.

$LL^{1c}$ represents an n2-valent alkane, an n2-valent alkene, an n2-valent alkyne, an n2-valent arene, an n2-valent heterocyclic group, a trivalent phosphoric acid group, a phosphanetriyl group, an isocyanurate group, or an n2-valent group formed by combining two or more groups and bonds selected from the group consisting of the aforementioned groups, an alkylene group, an alkenylene group, an alkynylene group, an arylene group, —O—, —S—, —$NR^a$—, an ester bond, a thioester bond, an amide bond, a thioamide bond, and a sulfonyl group.

$R^a$ represents a hydrogen atom or a substituent.

$Y^4$, $Y^7$, $Y^{10}$, and $Y^{13}$ each represent a hydroxy group or an alkoxy group. $Y^5$, $Y^6$, $Y^8$, $Y^9$, $Y^{11}$, $Y^{12}$, $Y^{14}$, and $Y^{15}$ each represent a hydroxy group, an alkoxy group, an alkyl group, or a ketoxime group.

n2 is 3 or 4.

However, the compound represented by any of general formulae (2) to (4) includes none of a vinyl silane coupling agent, a (meth)acrylic silane coupling agent, an epoxy silane coupling agent, an amino silane coupling agent, and a sulfanyl silane coupling agent.

<4>

The flexible tube for an endoscope according to any one of <1>to <3>, wherein the aluminum alkoxide compound includes a compound represented by general formula (a) or (b) below.

General formula (a): $R^{1a}{}_{m1}—Al—(OR^{2a})_{3-m1}$

General formula (b): $O—[Al—(OR^{2a})_2]_2$ $R^{1a}$ represents a hydrogen atom, an alkyl group, a cycloalkyl group, an acyl group, an aryl group, or an unsaturated aliphatic group.

$R^{2a}$ represents a hydrogen atom, an alkyl group, a cycloalkyl group, an acyl group, an alkenyl group, an aryl group, a phosphonate group, or $—SO_2R^{S1}$. $R^{S1}$ represents a substituent.

m1 is an integer of 0 to 2.

<5>

The flexible tube for an endoscope according to <4>, wherein in general formulae (a) and (b), at least one of $OR^{2a}$ has an acetonato structure or an acetato structure.

<6>

The flexible tube for an endoscope according to any one of <1>to <5>, wherein the zirconium alkoxide compound includes a compound represented by general formula (c) or (d) below.

General formula (c): $R^{1b}{}_{m2}—Zr—(OR^{2b})_{4-m2}$

General formula (d): $O—[Zr—(OR^{2b})_3]_2$ $R^{1b}$ represents a hydrogen atom, an alkyl group, a cycloalkyl group, an acyl group, an aryl group, or an unsaturated aliphatic group.

$R^{2b}$ represents a hydrogen atom, an alkyl group, a cycloalkyl group, an acyl group, an alkenyl group, an aryl group, a phosphonate group, or $—SO_2R^{S2}$. $R^{S2}$ represents a substituent.

m2 is an integer of 0 to 3.

<7>

The flexible tube for an endoscope according to <6>, wherein in general formulae (c) and (d), at least one of $OR^{2b}$ has an acetonato structure, an acetato structure, or a lactato structure.

<8>

The flexible tube for an endoscope according to any one of <1>to <7>, wherein the titanium alkoxide compound includes a compound represented by general formula (e) or (f).

General formula (e): $R^{1c}{}_{m3}—Ti—(OR^{2c})_{4-m3}$

General formula (f): $O—[Ti—(OR^{2c})_3]_2$ $R^{1c}$ represents a hydrogen atom, an alkyl group, a cycloalkyl group, an acyl group, an aryl group, or an unsaturated aliphatic group.

$R^{2c}$ represents a hydrogen atom, an alkyl group, a cycloalkyl group, an acyl group, an alkenyl group, an aryl group, a phosphonate group, or $—SO_2R^{S3}$. $R^{S3}$ represents a substituent.

m3 is an integer of 0 to 3.

<9>

The flexible tube for an endoscope according to <8>, wherein the compound represented by general formula (e) or (f) includes at least one atom selected from the group consisting of N, P, and S.

<10>

The flexible tube for an endoscope according to any one of <1>to <9>, wherein the metal that constitutes the flexible-tube base is stainless steel.

<11>

The flexible tube for an endoscope according to any one of <1>to <10>, wherein the metal that constitutes the flexible-tube base has a passivation film on a surface of the metal.

<12>

An endoscopic medical device having the flexible tube for an endoscope according to any one of <1>to <11>.

<13>

A method for producing a flexible tube for an endoscope, the method including:

a step of forming, on at least an outer periphery of a flexible-tube base containing metal as a constituent material, a primer layer including at least one of a silane coupling agent, an aluminum alkoxide compound, a zirconium alkoxide compound, or a titanium alkoxide compound; and a step of forming, on the primer layer formed on the outer periphery of the flexible-tube base, a cover layer using a cover layer-forming material that includes a polyester having a naphthalene structure.

However, the silane coupling agent includes none of a vinyl silane coupling agent, a (meth)acrylic silane coupling agent, an epoxy silane coupling agent, an amino silane coupling agent, and a sulfanyl silane coupling agent.

<14>

A method for producing an endoscopic medical device, the method including:

a step of obtaining a flexible tube for an endoscope by the method for producing a flexible tube for an endoscope according to <13>; and a step of incorporating the obtained flexible tube for an endoscope into an insertion section of an endoscopic medical device.

<15>

A method for producing an endoscopic medical device, the method including: incorporating the flexible tube for an endoscope according to any one of <1>to <11>into an insertion section of an endoscopic medical device.

In the description of the present specification, the term "metal alkoxide compound (specifically, for example, an aluminum alkoxide compound, a zirconium alkoxide compound, and a titanium alkoxide compound described later)" means a compound having a structure in which at least one alkoxy group is bonded to a metal atom. The alkoxy group may have a substituent. The substituent may be monovalent or divalent (for example, an alkylidene group). Furthermore, two alkoxy groups bonded to one metal atom may be bonded together to form a ring.

In the description of the present specification, unless otherwise specified, when a general formula representing a compound has a plurality of groups denoted by the same symbol, these may be the same or different from each other. A group (for example, an alkyl group) denoted by each group may further have a substituent.

In the description of the present specification, a numerical range represented using "to" mean a range that includes a numerical value before "to" as a lower limit and a numerical value after "to" as an upper limit.

The flexible tube for an endoscope according to the present invention can sufficiently maintain adhesiveness between the flexible-tube base and the cover layer covering the flexible-tube base even when a bending movement is repeated, and is unlikely to be subjected to a decrease in adhesiveness between the flexible-tube base and the cover layer even when subjected to strong sterilization treatment with ozone water. The endoscopic medical device according to the present invention is a device including the flexible tube for an endoscope, the flexible tube having the above good characteristics. The method for producing a flexible tube for an endoscope according to the present invention enables the production of the flexible tube for an endoscope according to the present invention, the flexible tube having the above characteristics. The method for producing an endoscopic medical device according to the present invention enables the production of an endoscopic medical device including the flexible tube for an endoscope according to the present invention, the flexible tube having the above characteristics.

DESCRIPTION OF THE PREFERRED EMBODIMENTS

Figure 1:
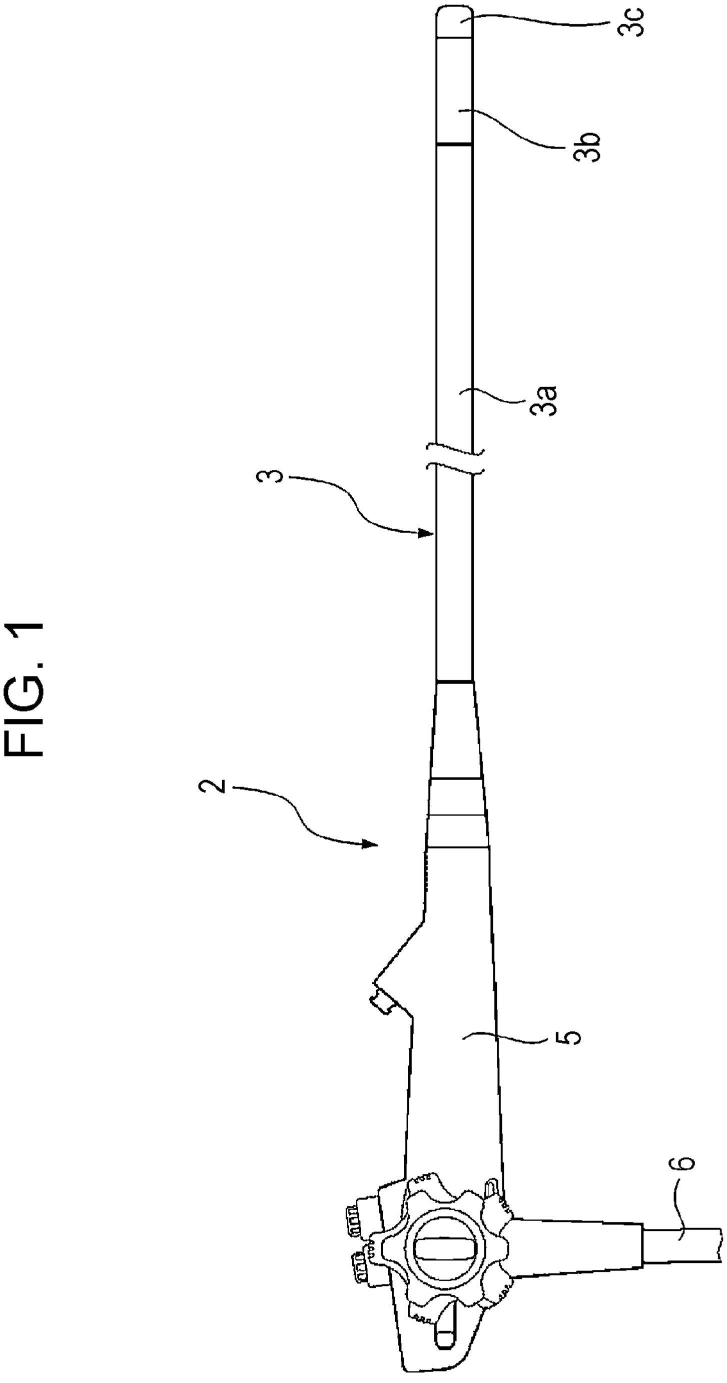
FIG. 1 is an external view illustrating a configuration of an electronic endoscope.

A flexible tube for an endoscope (a flexible tube for an endoscope may be hereinafter simply referred to as a "flexible tube") according to the present invention is a flexible tube for an endoscope, the flexible tube having a flexible-tube base containing metal as a constituent material, a cover layer covering an outer periphery of the flexible-tube base, and a primer layer disposed between the flexible-tube base and the cover layer and including at least one of a silane coupling agent, an aluminum alkoxide compound, a zirconium alkoxide compound, or a titanium alkoxide compound, in which the cover layer includes, at least on a side in contact with the primer layer, a polyester having a naphthalene structure.

However, in the present invention, a simple term "silane coupling agent" includes none of a vinyl silane coupling agent, a (meth)acrylic silane coupling agent, an epoxy silane coupling agent, an amino silane coupling agent, and a sulfanyl silane coupling agent.

Primer Layer

In the present invention, a primer layer (not illustrated) is disposed on an outer periphery of a flexible-tube base. By providing this primer layer, it is possible to effectively enhance the adhesiveness between the flexible-tube base and a cover layer provided to cover the outer periphery of the flexible-tube base. The cover layer will be described later. In the present invention, the primer layer includes at least one of a silane coupling agent, an aluminum alkoxide compound, a zirconium alkoxide compound, or a titanium alkoxide compound and preferably includes at least one of an aluminum alkoxide compound, a zirconium alkoxide compound, or a titanium alkoxide compound, and more preferably includes a titanium alkoxide compound in view of peeling resistance and sterilization durability.

Silane Coupling Agent

As the silane coupling agent used in the present invention, typical silane coupling agents applicable to a primer layer of a flexible tube for an endoscope can be widely employed. However, this silane coupling agent includes none of a vinyl silane coupling agent, a (meth)acrylic silane coupling agent, an epoxy silane coupling agent, an amino silane coupling agent, and a sulfanyl silane coupling agent. As described in Examples described later, the inventors of the present invention have made it clear as an experimental fact that the intended effect cannot be obtained when any of these silane coupling agents is used. The "vinyl silane coupling agent" refers to a silane coupling agent which has a vinyl group ($CH_2{=}CH-$) and in which the vinyl group is directly bonded to a silicon atom. That is, for example, in general formula (2) described below, "$LL^{1a}$-$L^2$-" does not represent "$CH_2{=}CH-$". The "(meth)acrylic silane coupling agent" refers to a silane coupling agent having a (meth)acryloyl group.

The "epoxy silane coupling agent" refers to a silane coupling agent having an epoxy group.

The "amino silane coupling agent" refers to a silane coupling agent having an amino group ($-NH_2$ group).

The "sulfanyl silane coupling agent" refers to a silane coupling agent having a sulfanyl group (mercapto group) ($-SH$ group).

The silane coupling agent preferably includes a compound represented by general formula (1) below. The proportion of the content of the compound represented by general formula (1) below in the silane coupling agent is not particularly limited, can be, for example, 60% by mass or more, is preferably 80% by mass or more, more preferably 90% by mass or more, still more preferably 95% by mass or more, and may be 100% by mass.

General formula (1)

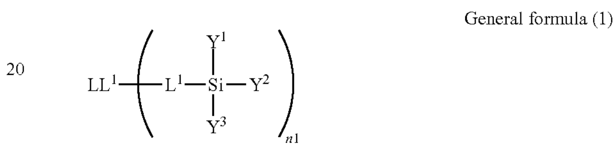

In the formula, $LL^1$ represents a monovalent substituent or an n1-valent linking group. $L^1$ represents a single bond or a divalent linking group. $Y^1$ to $Y^3$ each represent a substituent. n1 is an integer of 1 to 4. ($LL^1$ represents a monovalent substituent when n1 is 1, and $LL^1$ represents a divalent to tetravalent linking group when n1 is an integer of 2 to 4.)

However, at least one of $Y^1$ to $Y^3$ is a group selected from the group consisting of alkoxy groups and a hydroxy group. When n1 is 1, $LL^1$, $LL^1$-$L^1$, and $Y^1$ to $Y^3$ do not simultaneously represent groups selected from the group consisting of alkoxy groups and a hydroxy group.

The compound represented by general formula (1) above preferably includes a compound represented by any of general formulae (2) to (4) below and more preferably includes a compound represented by general formula (3) or (4) below in view of peeling resistance and sterilization durability.

General formula (2)

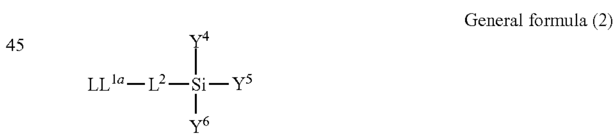

General formula (3)

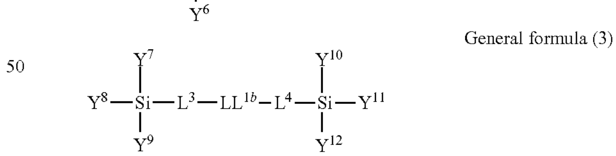

General formula (4)

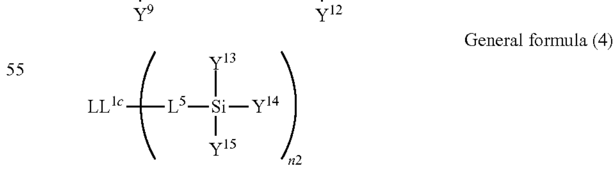

In the formulae, $LL^{1a}$ represents a hydrogen atom, an alicyclic group, a heterocyclic group, a hydroxy group, a sulfanyl group, an isocyanato group, a thiocyanato group, a ureido group, a cyano group, an acid anhydride group, an azide group, a carboxy group, an acyl group, a thiocarbamoyl group, a phosphoric acid group, a phosphanyl group, a sulfonic acid group, or a sulfamoyl group.

$L^2$ represents a single bond, an alkylene group, an alkenylene group, an alkynylene group, an arylene group, —O—, —S—, —$NR^a$—, an ester bond (—C(=O)—O— or —O—C(=O)—), a thioester bond (—S(=O)—O— or —O—S(=O)—), an amide bond (—NH—C(=O)— or —C(=O)—NH—), a thioamide bond (—NH—S(=O)— or —S(=O)—NH—), a sulfonyl group, or a divalent group formed by combining two or more selected from the group consisting of the aforementioned groups and bonds.

$L^3$ to $L^5$ each represent a single bond, an alkylene group, an alkenylene group, an alkynylene group, an arylene group, —O—, —S—, —$NR^a$—, an ester bond, a thioester bond, an amide bond, a thioamide bond, a urea bond, a thiourea bond, a sulfonyl group, or a divalent group formed by combining two or more selected from the group consisting of the aforementioned groups and bonds.

$LL^{1b}$ represents a single bond, an alkylene group, an alkenylene group, an alkynylene group, an arylene group, —O—, —S—, —$NR^a$—, a divalent heterocyclic group, an amide bond, an ester bond, a thioester bond, a divalent phosphoric acid group (a divalent group formed by removing two hydrogen atoms from phosphoric acid), a phosphanediyl group, a sulfonyl group, or a divalent group formed by combining two or more selected from the group consisting of the aforementioned groups and bonds.

$LL^{1c}$ represents an n2-valent alkane, an n2-valent alkene, an n2-valent alkyne, an n2-valent arene, an n2-valent heterocyclic group, a trivalent phosphoric acid group, a phosphanetriyl group, an isocyanurate group, or an n2-valent group formed by combining two or more groups and bonds selected from the group consisting of the aforementioned groups, an alkylene group, an alkenylene group, an alkynylene group, an arylene group, —O—, —S—, —$NR^a$—, an ester bond, a thioester bond, an amide bond, a thioamide bond, and a sulfonyl group.

$R^a$ represents a hydrogen atom or a substituent and preferably represents a hydrogen atom.

$Y^4$, $Y^7$, $Y^{10}$, and $Y^{13}$ each represent a hydroxy group or an alkoxy group. $Y^5$, $Y^6$, $Y^8$, $Y^9$, $Y^{11}$, $Y^{12}$, $Y^{14}$, and $Y^{15}$ each represent a hydroxy group, an alkoxy group, an alkyl group, or a ketoxime group.

n2 is 3 or 4.

Note that a partial structure ("—NH—") taken from an amide bond is not interpreted as —$NR^a$— and that a partial structure ("—O—") taken from an ester bond is not interpreted as —O—. Even in the case where an acid anhydride group has a heterocyclic ring, this acid anhydride group is not interpreted as a heterocyclic group.

With regard to the structure corresponding to $LL^{1a}$-$L^2$- in the compound represented by general formula (2), structures are applied in the order of $LL^{1a}$ and $L^2$.

Provided that there is a group that can be interpreted as both a group represented by $LL^{1a}$ and a combination of a group represented by $LL^{1a}$ or the like and a bond represented by $L^2$ (for example, a hydroxy group, a sulfanyl group, a thiocyanato group, a ureido group, an acid anhydride group, a carboxy group, an acyl group, or a carbamoyl group), the group is preferentially interpreted as a group represented by $LL^{1a}$. When $L^2$ is a combination of two or more of an alkylene group, an alkenylene group, an alkynylene group, an arylene group, —O—, —S—, —$NR^a$—, an ester bond, a thioester bond, an amide bond, a thioamide bond, and a sulfonyl group, the $L^2$ is interpreted such that the number of groups (bonds) constituting this combination is minimized.

When Exemplary compound K-11 shown below is explained as an example, $LL^{1a}$ represents a thiocyanato group, and $L^2$ represents an alkylene group.

With regard to the structure corresponding to -$L^3$-$LL^{1b}$-$L^4$- in the compound represented by general formula (3), structures are applied in the order of $L^3$, $L^4$, and $LL^{1b}$. In this case, $L^3$ and $L^4$ are selected so as to minimize the number of combinations of the groups (bonds) represented by $L^3$ and the number of combinations of the groups (bonds) represented by $L^4$.

When Exemplary compound K-24 shown below is explained as an example, $L^3$ represents an alkylene group, $L^4$ represents an alkylene group, and $LL^{1b}$ represents a combination of an ester bond and —O—. When Exemplary compound K-25 shown below is explained as an example, $L^3$ represents an alkylene group, $L^4$ represents an alkylene group, and $LL^{1b}$ represents a combination of two ester bonds and an alkenylene group.

However, in the case where the structure corresponding to -$L^3$-$LL^{1b}$ -$L^4$- is one type of group (for example, an alkylene group), it is interpreted that $L^3$ and $L^4$ each represent a single bond.

With regard to the structure corresponding to $LL^{1c}$-$(L^5)_{n2}$- in the compound represented by general formula (4), structures are applied in the order of $L^5$ and $LL^{1c}$. In this case, $L^5$ is selected so as to minimize the number of combinations of the group or the like represented by $L^5$.

However, in the case where the structure corresponding to $LL^{1c}$-$(L^5)_{n2}$- is one type of group (for example, an n2-valent alkane), it is interpreted that $L^5$, the number of which is n2, each represent a single bond.

The alicyclic group that can be employed as $LL^{1a}$ is preferably an alicyclic hydrocarbon group, and the alicyclic hydrocarbon group may be any of a cycloalkyl group, a cycloalkenyl group, and a cycloalkynyl group. The number of carbon atoms of the cycloalkyl group is preferably 3 to 20, more preferably 4 to 15, and still more preferably 5 to 10. The number of carbon atoms of the cycloalkenyl group and the number of carbon atoms of the cycloalkynyl group are each preferably 6 to 20, more preferably 6 to 15, more preferably 6 to 10, and still more preferably 6.

The heterocyclic ring constituting the heterocyclic group that can be employed as $LL^{1a}$ may be a saturated or unsaturated aliphatic heterocyclic ring or an aromatic heterocyclic ring and may be a monocycle or a fused ring. The heterocyclic ring may be a bridged ring. Examples of heteroatoms that constitute the heterocyclic ring include an oxygen atom, a nitrogen atom, and a sulfur atom. The number of heteroatoms included in one heterocyclic ring is not particularly limited, but is preferably 1 to 3 and more preferably 1 or 2. The number of carbon atoms of the heterocyclic ring is preferably 2 to 10 and more preferably 4 or 5. The heterocyclic ring is preferably a three- to seven-membered ring, more preferably a three- to six-membered ring, and still more preferably a three- to five-membered ring. Specific examples of the heterocyclic ring include an epoxy ring, a 3,4-epoxycyclohexane ring, a furan ring, and a thiophene ring.

The number of carbon atoms of the acyl group that can be employed as $LL^{1a}$ is preferably 0 to 40, more preferably 0 to 30, more preferably 0 to 20, more preferably 0 to 15, and still more preferably 0 to 10. In the present invention, the acyl group includes a formyl group, a carbamoyl group, an alkyl carbonyl group, an alkenyl carbonyl group, and an aryl carbonyl group.

The acid anhydride group that can be employed as $LL^{1a}$ is preferably a monovalent group having a carboxylic acid anhydride structure. Examples thereof include a maleic anhydride group, a succinic anhydride group, a glutaric anhydride group, an adipic anhydride group, and a citraconic anhydride group, such as 3,4-dihydro-2,5-furandionyl.

The alkylene group that can be employed as $L^2$ may be linear or branched. The number of carbon atoms of the alkylene group is preferably 1 to 30, more preferably 1 to 25, more preferably 1 to 20, and more preferably 1 to 15. Specific examples of the alkylene group include methylene, ethylene, isopropylene, butylene, pentylene, cyclohexylene, heptylene, octylene, nonylene, decylene, and undecylene.

The alkenylene group that can be employed as $L^2$ may be linear or branched. The number of carbon atoms of the alkenylene group is preferably 2 to 20, more preferably 2 to 15, more preferably 2 to 10, and still more preferably 2 to 6. Specific examples of the alkenylene group include ethenylene and propenylene.

The alkynylene group that can be employed as $L^2$ may be linear or branched. The number of carbon atoms of the alkynylene group is preferably 2 to 20, more preferably 2 to 15, more preferably 2 to 10, and still more preferably 2 to 6. Specific examples of the alkynylene group include ethynylene and propynylene.

The number of carbon atoms of the arylene group that can be employed as $L^2$ is preferably 6 to 20, more preferably 6 to 15, more preferably 6 to 12, and still more preferably 6 to 10. Specific examples of the arylene group include phenylene and naphthylene.

Examples of the substituent in $R^a$ of —$NR^a$— that can be employed as $L^2$ include alkyl groups (preferably having 1 to 12 carbon atoms and more preferably having 1 to 8 carbon atoms), alkenyl groups (preferably having 2 to 12 carbon atoms and more preferably having 2 to 8 carbon atoms), alkynyl groups (preferably having 2 to 12 carbon atoms and more preferably having 2 to 8 carbon atoms), aryl groups (preferably having 6 to 20 carbon atoms and more preferably having 6 to 10 carbon atoms), and heterocyclic groups. Examples of the heterocyclic ring constituting the heterocyclic group that can be employed as $R^a$ include the heterocyclic rings constituting the heterocyclic group that can be employed as $LL^{1a}$, and preferred forms thereof are also the same as the preferred forms of the heterocyclic group that can be employed as $LL^{1a}$.

An example of —$NR^a$— is —NH—.

The number of groups and bonds combined and constituting the divalent group that is formed by combining two or more selected from the group consisting of the aforementioned groups and bonds and that can be employed as $L^2$ (hereinafter also referred to as a "group that is formed by a combination and can be employed as $L^2$") is preferably 2 to 8, more preferably 2 to 6, and still more preferably 2 to 4.

The molecular weight of the group that is formed by a combination and can be employed as $L^2$ is preferably 20 to 1,000, more preferably 30 to 500, and still more preferably 40 to 200.

Examples of the group that is formed by a combination and can be employed as $L^2$ include a urea bond, a thiourea bond, a carbamate group, a sulfonamide bond, arylene-alkylene, —O-alkylene, $NR^a$-alkylene, amide bond-alkylene, —S-alkylene, alkylene-O-amide bond-alkylene, alkylene-amide bond-alkylene, alkenylene-amide bond-alkylene, alkylene-ester bond-alkylene, arylene-ester bond-alkylene, -(alkylene-O)-, alkylene-O-(alkylene-O)-alkylene (where each "(alkylene-O)" represents a repeating unit), arylene-sulfonyl-O-alkylene, and ester bond-alkylene (where the term "group" is omitted, and hereinafter, a similar description may be made).

Examples of the alkylene groups, the alkenylene groups, the alkynylene groups, the arylene groups, and —$NR^a$— that can be employed as $L^3$ to $L^5$ include the alkylene groups, the alkenylene groups, the alkynylene groups, the arylene groups, and —$NR^a$— that can be employed as $L^2$, and preferred forms thereof are also the same as the preferred forms of the alkylene groups, the alkenylene groups, the alkynylene groups, the arylene groups, and —$NR^a$— that can be employed as $L^2$.

The alkylene group that can be employed as $LL^{1b}$ may be linear, branched, or cyclic.

The number of carbon atoms of the alkylene group is preferably 1 to 30, more preferably 1 to 25, more preferably 1 to 20, and still more preferably 1 to 15. Specific examples of the alkylene group include methylene, ethylene, isopropylene, butylene, pentylene, cyclohexylene, heptylene, octylene, nonylene, decylene, and undecylene.

The alkenylene group that can be employed as $LL^{1b}$ may be linear, branched, or cyclic. The number of carbon atoms of the alkenylene group is preferably 2 to 20, more preferably 2 to 15, more preferably 2 to 10, and still more preferably 2 to 6. Specific examples of the alkenylene group include ethenylene and propenylene.

The alkynylene group that can be employed as $LL^{1b}$ may be linear, branched, or cyclic. The number of carbon atoms of the alkynylene group is preferably 2 to 20, more preferably 2 to 15, more preferably 2 to 10, and still more preferably 2 to 6. Specific examples of the alkynylene group include ethynylene and propynylene.

Examples of the arylene group that can be employed as $LL^{1b}$ include the arylene groups that can be employed as $L^2$, and preferred forms thereof are also the same as the preferred forms of the arylene group that can be employed as $L^2$.

Examples of the heterocyclic ring constituting the divalent heterocyclic group that can be employed as $LL^{1b}$ include the heterocyclic rings constituting the heterocyclic group that can be employed as $LL^{1a}$, and preferred forms thereof are also the same as the preferred forms of the heterocyclic group that can be employed as $LL^{1a}$. Examples of —$NR^a$— that can be employed as $LL^{1b}$ include —$NR^a$— that can be employed as $L^2$, and preferred forms thereof are also the same as the preferred forms of —$NR^a$— that can be employed as $L^2$.

The number of groups and bonds combined and constituting the divalent group that is formed by combining two or more selected from the group consisting of the aforementioned groups and bonds and that can be employed as $LL^{1b}$ (hereinafter also referred to as a "group that is formed by a combination and can be employed as $LL^{1b}$") is preferably 2 to 8, more preferably 2 to 6, and still more preferably 2 to 4.

The molecular weight of the group that is formed by a combination and can be employed as $LL^{1b}$ is preferably 20 to 1,000, more preferably 30 to 500, and still more preferably 40 to 200.

Examples of the group that is formed by a combination and can be employed as $LL^{1b}$ include a urea bond, a carbonate group, a sulfonamide bond, a disulfide bond, ester bond-alkenylene-ester bond, -(alkylene-O)-, and —O-(alkylene-O)- (where each "(alkylene-O)" represents a repeating unit).

Among the n2-valent alkanes that can be employed as $LL^{1c}$, a trivalent alkane, that is, an alkanetriyl group preferably has 1 to 20 carbon atoms, more preferably 3 to 15 carbon atoms, more preferably 4 to 12 carbon atoms, and still more preferably 5 to 10 carbon atoms.

Among the n2-valent alkanes that can be employed as $LL^{1c}$, a tetravalent alkane, that is, an alkanetetrayl group preferably has 1 to 20 carbon atoms, more preferably 3 to 15 carbon atoms, more preferably 4 to 12 carbon atoms, and still more preferably 5 to 10 carbon atoms.

Among the n2-valent alkenes that can be employed as $LL^{1c}$, a trivalent alkene, that is, an alkenetriyl group preferably has 2 to 20 carbon atoms, more preferably 3 to 15 carbon atoms, more preferably 4 to 12 carbon atoms, and still more preferably 5 to 10 carbon atoms.

Among the n2-valent alkenes that can be employed as $LL^{1c}$, a tetravalent alkene, that is, an alkenetetrayl group preferably has 2 to 20 carbon atoms, more preferably 3 to 15 carbon atoms, more preferably 4 to 12 carbon atoms, and still more preferably 5 to 10 carbon atoms.

Among the n2-valent alkynes that can be employed as $LL^{1c}$, a trivalent alkyne, that is, an alkynetriyl group preferably has 3 to 20 carbon atoms, more preferably 3 to 15 carbon atoms, more preferably 4 to 12 carbon atoms, and still more preferably 5 to 10 carbon atoms.

Among the n2-valent alkynes that can be employed as $LL^{1c}$, a tetravalent alkyne, that is, an alkynetetrayl group preferably has 3 to 20 carbon atoms, more preferably 3 to 15 carbon atoms, more preferably 4 to 12 carbon atoms, and still more preferably 5 to 10 carbon atoms.

Among the n2-valent arenes that can be employed as $LL^{1c}$, a trivalent arene, that is, an arenetriyl group preferably has 6 to 20 carbon atoms, more preferably 6 to 15 carbon atoms, more preferably 6 to 12 carbon atoms, and still more preferably 6 to 10 carbon atoms. Specific examples of the arenetriyl group include benzenetriyl and naphthalenetriyl.

Among the n2-valent arenes that can be employed as $LL^{1c}$, a tetravalent arene, that is, an arenetetrayl group preferably has 6 to 20 carbon atoms, more preferably 6 to 15 carbon atoms, more preferably 6 to 12 carbon atoms, and still more preferably 6 to 10 carbon atoms. Specific examples of the arenetetrayl group include benzenetetrayl and naphthalenetetrayl.

Examples of the heterocyclic ring constituting the n2-valent heterocyclic group that can be employed as $LL^{1c}$ include the heterocyclic ring constituting the heterocyclic group that can be employed as $LL^{1a}$, and preferred forms thereof are also the same as the preferred forms of the heterocyclic ring that can be employed as $LL^{1a}$. Examples of $—NR^a—$ that can be employed as $LL^{1c}$ include $—NR^a—$ that can be employed as $L^2$, and preferred forms thereof are also the same as the preferred forms of $—NR^a—$ that can be employed as $L^2$.

The number of groups and bonds combined and constituting the n2-valent group that is formed by combining two or more groups and bonds selected from the group consisting of the aforementioned groups, alkylene groups, alkenylene groups, alkynylene groups, arylene groups, —O—, —S—, $—NR^a—$, an ester bond, a thioester bond, an amide bond, a thioamide bond, and a sulfonyl group and that can be employed as $LL^{1c}$ (hereinafter also referred to as a "group that is formed by a combination and can be employed as $LL^{1c}$") is preferably 2 to 8, more preferably 2 to 6, and still more preferably 2 to 4.

The molecular weight of the group that is formed by a combination and can be employed as $LL^{1c}$ is preferably 20 to 1,000, more preferably 30 to 500, and still more preferably 40 to 200.

Examples of the group that is formed by a combination and can be employed as $LL^{1c}$ include a glycerol group, a trimethylolpropyl group, a 1,3,5-triazine group, and an isocyanuric group (1,3 ,5-triazine-2,4,6(1H,3H,5H)-trione-1,3,5-triyl group).

The alkyl group constituting the alkoxy group that can be employed as $Y^4$ to $Y^{15}$ may be linear, branched, or cyclic and may have these forms in combination. In the present invention, this alkyl group is preferably a linear alkyl group. The number of carbon atoms of the alkyl group constituting the alkoxy group is preferably 1 to 15, more preferably 1 to 10, more preferably 1 to 5, and still more preferably 1 or 2. Specific examples of the alkyl group constituting the alkoxy group include methyl, ethyl, propyl, t-butyl, pentyl, and cyclohexyl.

Examples of the alkyl groups that can be employed as $Y^5$, $Y^6$, $Y^8$, $Y^9$, $Y^{11}$, $Y^{12}$, $Y^{14}$, and $Y^{15}$ include the alkyl groups constituting the alkoxy groups that can be employed as $Y^4$ to $Y^{15}$, and preferred forms thereof are also the same as the preferred forms of the alkyl groups constituting the alkoxy groups that can be employed as $Y^4$ to $Y^{'5}$.

The ketoxime group is a substituent having the following structure.

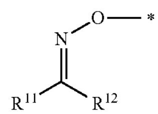

In the above structure, $R^{11}$ and $R^{12}$ each represent a substituent, and * represents a bonding site to a silicon atom.

Examples of the substituent that can be employed as $R^{11}$ and $R^{12}$ include the substituents in the $R^a$, and preferred forms thereof are also the same as the preferred forms of the substituent that can be employed as the $R^a$.

Examples of the ketoxime group include a dimethyl ketoxime group, a methyl ethyl ketoxime group, and a diethyl ketoxime group.

The silane coupling agent may have a substituent as long as the effects of the present invention are not impaired. Examples of the substituent include the above-described groups that can be employed as $LL^{1a}$, alkyl groups, alkenyl groups, alkynyl groups, and aryl groups. Examples of the substituent further include an unsubstituted silyl group and substituted silyl groups having no alkoxy group or hydroxy group as a substituent.

In general formula (2), $LL^{1a}$ or $L^2$ and at least one of $Y^5$ or $Y^6$ may be linked to each other to form a ring. The number of atoms constituting this ring is preferably 3 to 10, more preferably 4 to 8, and still more preferably 5 or 6.

In general formula (3), $LL^{1b}$ or $L^3$ and at least one of $Y^8$ or $Y^9$ may be linked to each other to form a ring. The number of atoms constituting this ring is preferably 3 to 10, more preferably 4 to 8, and still more preferably 5 or 6. $LL^{1b}$ or $L^4$ and at least one of or $Y^{12}$ may be linked to each other to form a ring. The number of atoms constituting this ring is preferably 3 to 10, more preferably 4 to 8, and still more preferably 5 or 6. Two or more of these rings may be formed at the same time.

In general formula (4), $LL^{1c}$ or $L^5$ and at least one of $Y^{13}$ or $Y^{14}$ may be linked to each other to form a ring. The number of atoms constituting this ring is preferably 3 to 10, more preferably 4 to 8, and still more preferably 5 or 6.

In general formula (2), $LL^{1a}$ preferably represents a hydrogen atom, an alicyclic group, a heterocyclic group, a hydroxy group, a sulfanyl group, a thiocyanato group, an acid anhydride group, a carboxy group, an acyl group, or a sulfonic acid group. $L^2$ preferably represents an alkylene group, an alkenylene group, an alkynylene group, an arylene group, —O—, —S—, $—NR^a—$, an ester bond, a thioester bond, an amide bond, a sulfonyl group, or a divalent group formed by combining two or more selected from the group consisting of the aforementioned groups and bonds.

In general formula (2), $LL^{1a}$ preferably represents a hydrogen atom, a hydroxy group, a carboxylic anhydride group, a carboxy group, an acyl group, or a sulfonic acid group. $L^2$ more preferably represents an alkylene group, an alkenylene group, —O—, —$NR^a$—, an ester bond, an amide bond, or a divalent group formed by combining two or more selected from the group consisting of the aforementioned groups and bonds.

Specific examples of $LL^{1a}$-$L^2$- include hydrogen atom-alkenylene (provided that hydrogen atom-CH═CH— is excluded), hydrogen atom-arylene-alkylene, alicyclic-alkylene, heterocyclic-alkylene, acyl-O-alkylene, acyl-$NR^a$-alkylene, sulfanyl-alkylene, heterocyclic-S-alkylene, thiocyanato-alkylene, hydroxy-alkylene, hydroxy-alkylene-amide bond-alkylene, carboxy-alkylene, acyl-alkylene-amide bond-alkylene, acid anhydride-alkylene, hydrogen atom-arylene-ester bond-alkylene, hydrogen atom-alkylene-ester bond-alkylene, hydrogen atom-alkylene-O-(alkylene-O)-alkylene, sulfonic-alkylene, and hydrogen atom-arylene-sulfonyl-O-alkylene.

In general formula (2), at least two of $Y^4$ to $Y^6$ are each preferably an alkoxy group or a hydroxy group, and all of $Y^4$ to $Y^6$ are each more preferably an alkoxy group or a hydroxy group.

In general formula (3), $LL^{1b}$ preferably represents an alkylene group, an alkenylene group, an arylene group, —O—, —S—, an ester bond, a thioester bond, an amide bond, a sulfonyl group, or a divalent group formed by combining two or more selected from the group consisting of the aforementioned groups and bonds. $L^3$ and $L^4$ each preferably represent a single bond, an alkylene group, an alkenylene group, an alkynylene group, an arylene group, —O—, —S—, an ester bond, a thioester bond, an amide bond, a sulfonyl group, or a divalent group formed by combining two or more selected from the group consisting of the aforementioned groups and bonds, and more preferably represent a single bond, an alkylene group, an alkenylene group, —O—, an ester bond, or an amide bond.

Specific examples of -$L^3$-$LL^{1b}$ -$L^4$ include alkylene, alkylene-ester bond-O-alkylene, alkylene-ester bond-alkenylene-ester bond-alkylene, alkylene-O-(alkylene-O)-alkylene, alkylene-arylene-alkylene, and alkylene-S—S-alkylene.

In general formula (3), at least two of $Y^7$ to $Y^9$ are each preferably an alkoxy group or a hydroxy group.

In general formula (3), at least two of $Y^{10}$ to $Y^{12}$ are each preferably an alkoxy group or a hydroxy group.

In general formula (4), n2 is preferably 3, and $LL^{1c}$ preferably represents an isocyanurate group. $L^5$ preferably represents an alkylene group.

In general formula (4), at least two of $Y^{13}$ to $Y^{15}$ are each preferably an alkoxy group or a hydroxy group, and all of $Y^{13}$ to $Y^{15}$ are each more preferably an alkoxy group or a hydroxy group.

In general formula (4), n2 is preferably 3.

The compound represented by general formula (1) and used in the present invention contributes to adhesion between the flexible-tube base and the cover layer in a monomolecular form. The thickness of the primer layer is significantly smaller than that of a typical adhesive layer (in other words, the concept of the thickness cannot be recalled). That is, the primer layer including the compound represented by general formula (1) differs from such an adhesive layer that requires a certain layer thickness and softness for adhesion between the flexible-tube base and the cover layer. Therefore, in fact, the primer layer does not affect the resilience of the flexible tube, and thus the flexible tube according to the present invention also has good resilience.

In the present invention, the expression "include a silane coupling agent" is meant to include a form in which a silane coupling agent is included in a state of having reacted with the flexible-tube base and a form in which a silane coupling agent is included in a state of having reacted with the cover layer. Specifically, for example, at least a portion of a silane coupling agent is hydrolyzed, so that a hydroxy group is exposed, and the silane coupling agent in this state can be present in a form where the silane coupling agent reacts with the metal constituting the flexible-tube base or reacts with a group on the surface of the cover layer.

Alternatively, for example, when the primer layer is formed by using a coating liquid, the pH of which has been adjusted to be acidic or alkaline as described later, a portion of the silane coupling agent may be present in the form of a salt or an ion. An example of the form of an ion is a form in which a group capable of forming an anion (anionic group) is present as an anion. An example of the form of a salt is a form in which the anionic group is present as a salt-type group having, as a counter cation, for example, an alkali metal ion such as a sodium ion or a potassium ion.

The same applies to metal alkoxide compounds described later.

Specific examples of the silane coupling agent are given below; however, the present invention is not limited to these.

In the structures below, Me represents methyl, and Et represents ethyl. The structure in the parentheses in compound K-20 represents a repeating unit with a number of repetitions of 6 to 9. The structure in the parentheses in compound K-26 represents a repeating unit with a number of repetitions of 6 to 9.

In the chemical structural formulae below, with regard to compounds that represent alkoxy groups as substituents bonded to a silicon atom, compounds having structures in which some or all of the alkoxy groups are hydroxy groups are also included in the specific examples of the silane coupling agent. In the exemplary compounds, R represents an alkyl group.

K-1

K-2

K-3

K-7

K-9

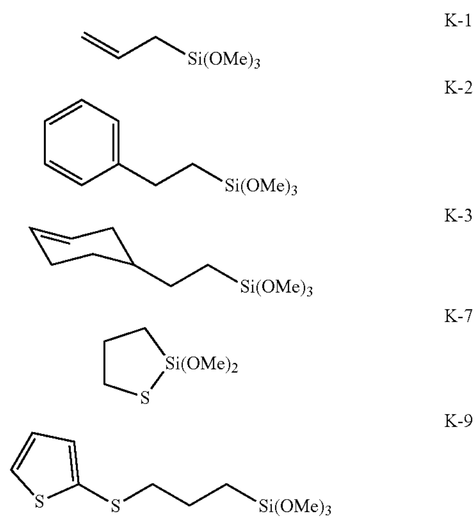

-continued

K-10

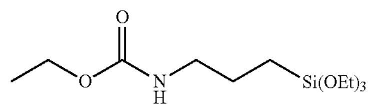

K-11

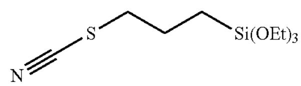

K-12

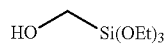

K-13

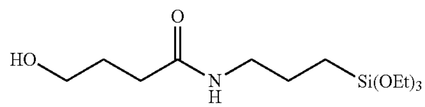

K-14

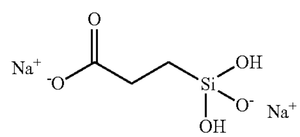

K-15

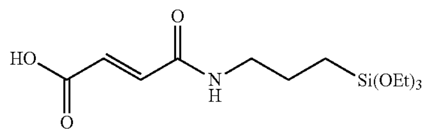

K-16

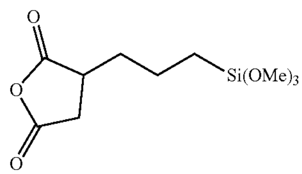

K-17

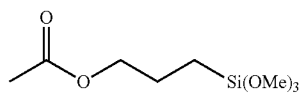

K-18

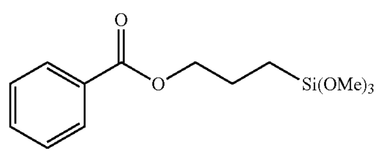

K-19

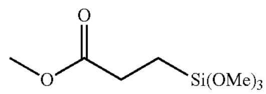

K-20

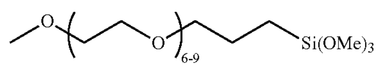

K-21

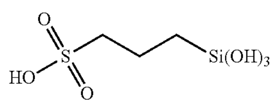

K-22

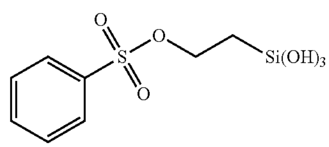

K-23

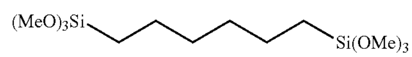

-continued

K-24

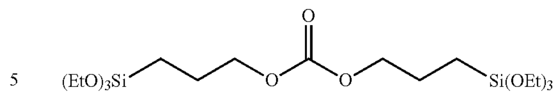

K-25

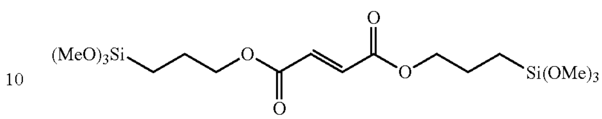

K-26

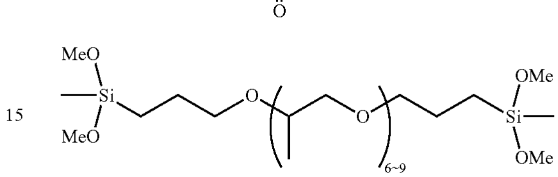

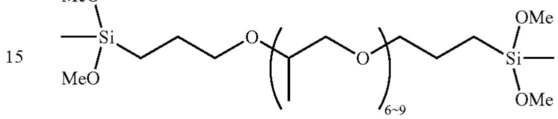

K-27

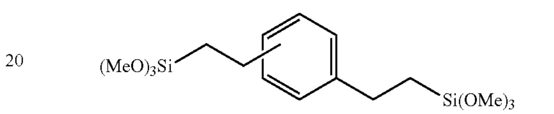

K-28

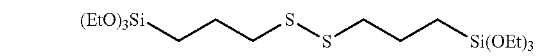

K-29

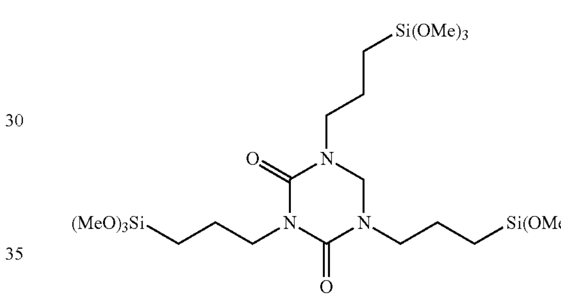

K-30

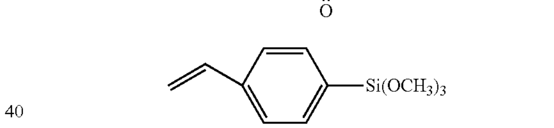

K-31

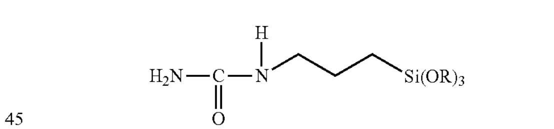

K-32

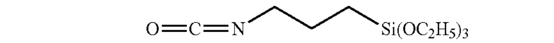

Aluminum Alkoxide Compound

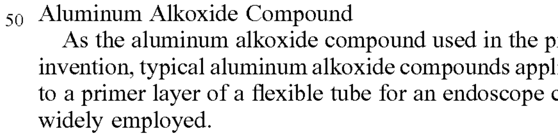

As the aluminum alkoxide compound used in the present invention, typical aluminum alkoxide compounds applicable to a primer layer of a flexible tube for an endoscope can be widely employed.

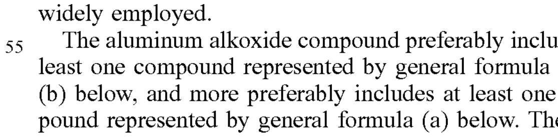

The aluminum alkoxide compound preferably includes at least one compound represented by general formula (a) or (b) below, and more preferably includes at least one compound represented by general formula (a) below. The proportion of the total content of the compound represented by the following general formula (a) or (b) in the aluminum alkoxide compound is not particularly limited, can be, for example, 60% by mass or more, is preferably 80% by mass or more, more preferably 90% by mass or more, still more preferably 95% by mass or more, and may be 100% by mass.

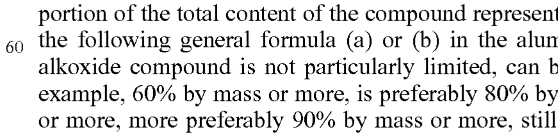

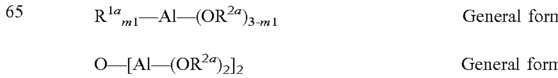

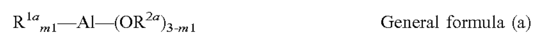

$R^{1a}_{m1}$—Al—$(OR^{2a})_{3-m1}$ General formula (a)

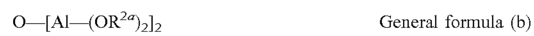

O—[Al—$(OR^{2a})_2]_2$ General formula (b)

$R^{1a}$ represents a hydrogen atom, an alkyl group, a cycloalkyl group, an acyl group, an aryl group, or an unsaturated aliphatic group.

The alkyl group that can be employed as $R^{1a}$ includes linear alkyl groups, branched alkyl groups, and aralkyl groups. The number of carbon atoms of the alkyl group is preferably 1 to 20, more preferably 1 to 15, still more preferably 1 to 10, and particularly preferably 1 to 8, and in the case of an aralkyl group, the number of carbon atom is preferably 7 to 30. Specific preferred examples of the alkyl group include methyl, ethyl, propyl, isopropyl, butyl, sec-butyl, isobutyl, tert-butyl, pentyl, hexyl, heptyl, octyl, decyl, tridecyl, octadecyl, benzyl, and phenethyl.

It is also preferred that the alkyl group that can be employed as $R^{1a}$ have an oxirane ring. The number of ring members of the cycloalkyl group in the epoxycycloalkyl group (that is, a cycloalkyl group having a structure in which an oxirane ring is fused thereto) that can be employed as $R^{1a}$ is preferably 4 to 8, more preferably 5 or 6, and still more preferably 6 (that is, an epoxycyclohexyl group).

It is also preferred that the alkyl group that can be employed as $R^{1a}$ have a group selected from the group consisting of an amino group, an isocyanato group, a mercapto group, an ethylenically unsaturated group, and an acid anhydride group.

The cycloalkyl group that can be employed as $R^{1a}$ preferably has 3 to 20 carbon atoms, more preferably 3 to 15 carbon atoms, still more preferably 3 to 10 carbon atoms, and particularly preferably 3 to 8 carbon atoms. Preferred specific examples of the cycloalkyl group include cyclopropyl, cyclopentyl, and cyclohexyl.

The acyl group that can be employed as $R^{1a}$ preferably has 2 to 40 carbon atoms, more preferably 2 to 30 carbon atoms, still more preferably 2 to 20 carbon atoms, and particularly preferably 2 to 18 carbon atoms.

The aryl group that can be employed as $R^{1a}$ preferably has 6 to 20 carbon atoms, more preferably 6 to 15 carbon atoms, still more preferably 6 to 12 carbon atoms, and particularly preferably 6 to 10 carbon atoms. Preferred specific examples of the aryl group include phenyl and naphthyl, and phenyl is more preferred.

The number of carbon-carbon unsaturated bonds of the unsaturated aliphatic group that can be employed as $R^{1a}$ is preferably 1 to 5, more preferably 1 to 3, still more preferably 1 or 2, and particularly preferably 1. The unsaturated aliphatic group may include a heteroatom and is also preferably a hydrocarbon group. When the unsaturated aliphatic group is a hydrocarbon group, the hydrocarbon group preferably has 2 to 20 carbon atoms, more preferably 2 to 15 carbon atoms, still more preferably 2 to 10 carbon atoms, even more preferably 2 to 8 carbon atoms, or preferably has 2 to 5 carbon atoms. More preferably, the unsaturated aliphatic group is an alkenyl group or an alkynyl group.

$R^{1a}$ is preferably a hydrogen atom, an alkyl group, a cycloalkyl group, or aryl group, and more preferably an alkyl group or a cycloalkyl group.

When the compound represented by general formula (a) has two or more $R^{1a}$, two $R^{1a}$ may be linked to each other to form a ring.

$R^{2a}$ represents a hydrogen atom, an alkyl group, a cycloalkyl group, an acyl group, an alkenyl group, an aryl group, a phosphonate group (phosphonic acid group), or $—SO_2R^{S1}$. $R^{S1}$ represents a substituent.

The alkyl group, the cycloalkyl group, the acyl group, and the aryl group that can be employed as $R^{2a}$ have the same meaning as the alkyl group, the cycloalkyl group, the acyl group, and the aryl group, respectively, that can be employed as $R^{1a}$, and preferred forms of each group are also the same. It is also preferred that the alkyl group that can be employed as $R^{2a}$ have an amino group as a substituent.

The alkenyl group that can be employed as $R^{2a}$ includes linear alkenyl groups and branched alkenyl groups. The alkenyl group preferably has 2 to 18 carbon atoms, more preferably 2 to 7 carbon atoms, and still more preferably 2 to 5 carbon atoms. Preferred specific examples of the alkenyl group include vinyl, allyl, butenyl, pentenyl, and hexenyl. The alkenyl group is preferably a substituted alkenyl group.

The phosphonate group that can be employed as $R^{2a}$ is a group represented by $—P(═O)(—OR^{P1})OR^{P2}$. $R^{P1}$ and $R^{P2}$ represent a hydrogen atom or a substituent. The substituent is preferably an alkyl group or a phosphonate group. The alkyl group that can be employed as $R^{P1}$ and $R^{P2}$ has the same meaning as the alkyl group that can be employed as $R^{1a}$ described above, and preferred forms of the alkyl group are also the same. The phosphonate group that can be employed as $R^{P1}$ and $R^{P2}$ has the same meaning as the phosphonate group that can be employed as $R^{2a}$, and preferred forms thereof are also the same. When $R^{P1}$ or $R^{P2}$ is a phosphonate group, $R^{P1}$ and $R^{P2}$ that form the phosphonate group are preferably alkyl groups.

In the phosphonate group that can be employed as $R^{2a}$, preferably, both $R^{P1}$ and $R^{P2}$ are alkyl groups, or $R^{P1}$ is a hydrogen atom and $R^{P2}$ is a phosphonate group.

Note that, since a phosphonate group and a phosphite group (phosphorous acid group) are tautomers, the term "phosphonate group" in the present invention is meant to include a phosphite group.

In $—SO_2R^{S1}$ that can be employed as $R^{2a}$, $R^{S1}$ is preferably an alkyl group or an aryl group. Preferred forms of the alkyl group and aryl group that can be employed as $R^{S1}$ include the preferred forms of the alkyl group and the aryl group, respectively, that can be employed as $R^{1a}$ described above. In particular, $R^{S1}$ is preferably a phenyl having an alkyl group as a substituent. Preferred forms of this alkyl group are the same as the preferred forms of the alkyl group that can be employed as $R^{1a}$ described above.

When the compound represented by general formula (a) has two or more $R^{2a}$, two $R^{2a}$ may be linked to each other to form a ring. In the compound represented by general formula (b), two $R^{2a}$ may be linked to each other to form a ring.

m1 is an integer of 0 to 2.

In general formulae (a) and (b) above, at least one of $OR^{2a}$ preferably has an acetonato structure. The acetonato structure refers to a structure coordinated to Al, the structure being formed by removing one hydrogen ion from acetone or a compound having a structure in which acetone has a substituent. The ligand atom coordinated to Al is typically an oxygen atom. The acetonato structure is preferably a structure that has an acetylacetone structure ("$CH_3—C(═O)—CH_2—C(═O)—CH_3$") as a basic structure and that is formed by removing one hydrogen ion from the basic structure and coordinating the resulting structure to Al using an oxygen atom as a ligand atom (i.e., an acetylacetonato structure). The phase "have an acetylacetone structure as a basic structure" is meant to include, besides the above acetylacetone structure, a structure obtained by replacing a hydrogen atom of the acetylacetone structure with a substituent. Examples of forms in which $OR^{2a}$ has an acetonato structure include the compounds A-2 and A-3 described later.

In general formulae (a) and (b) above, at least one of $OR^{2a}$ preferably has an acetato structure. In the present invention, the acetato structure refers to a structure coordinated to Al, the structure being formed by removing one hydrogen atom from acetic acid, an acetate, or a compound having a structure in which acetic acid or an acetate has a substituent (including forms in which the methyl group of acetic acid has an alkyl group as a substituent). The ligand atom coordinated to Al is typically an oxygen atom. The acetato structure is preferably a structure that has an alkyl acetoacetate structure ("$CH_3—C(=O)—CH_2—C(=O)—O—R_{alk}$" (where $R_{alk}$ represents an alkyl group (is preferably an alkyl group having 1 to 20 carbon atoms, may be an alkyl group having 1 to 10 carbon atoms, and is more preferably an alkyl group having 1 to 4 carbon atoms))) as a basic structure and that is formed by removing one hydrogen ion from the basic structure and coordinating the resulting structure to Al using an oxygen atom as a ligand atom (i.e., an alkyl acetoacetato structure). The phrase "have an alkyl acetoacetate structure as a basic structure" is meant to include, besides the above alkyl acetoacetate structure, a structure obtained by replacing a hydrogen atom of the alkyl acetoacetate structure with a substituent. Examples of forms in which $OR^{2a}$ has an acetato structure include compounds the A-3, A-4, and A-5 described later.

Each of the above groups that can be employed as $R^{1a}$ or $R^{2a}$ may have, as a substituent, an anionic group having a counter cation (salt-type substituent). The anionic group refers to a group capable of forming an anion. An example of an anionic group having a counter cation is a carboxylate ion group having an ammonium ion as a counter cation. In this case, it is sufficient that the counter cation be present in the compound represented by general formula (a) or (b) above such that the electric charge of the whole compound is zero. The same applies to a compound represented by general formula (c) or (d) and a compound represented by general formula (e) or (f). These compounds will be described later.

Specific examples of the aluminum alkoxide compound used in the present invention are given below; however, the present invention is not limited to these.

Aluminum triethylate
Aluminum triisopropylate
Aluminum tri-sec-butylate
Aluminum tris(ethylacetoacetate)
Ethylacetoacetate aluminum diisopropylate
Aluminum monoacetylacetonate bis(ethylacetoacetate)
Aluminum tris(acetylacetonate)
Diisopropoxyaluminum-9-octadecenylacetoacetate
Aluminum diisopropoxymonoethylacetoacetate
Mono-sec-butoxyaluminum diisopropylate
Diethylacetoacetate aluminum isopropylate
Aluminum bisethylacetoacetate monoacetylacetonate
Aluminum octadecylacetoacetate diisopropylate Zirconium Alkoxide Compound As the zirconium alkoxide compound used in the present invention, typical zirconium alkoxide compounds applicable to a primer layer of a flexible tube for an endoscope can be widely employed.

The zirconium alkoxide compound preferably includes at least one compound represented by general formula (c) or (d) below, and more preferably includes at least one compound represented by general formula (c) below. The proportion of the total content of the compound represented by the following general formula (c) or (d) in the zirconium alkoxide compound is not particularly limited, can be, for example, 60% by mass or more, is preferably 80% by mass or more, more preferably 90% by mass or more, still more preferably 95% by mass or more, and may be 100% by mass.

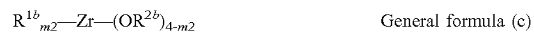

$R^{1b}{}_{m2}—Zr—(OR^{2b})_{4-m2}$ General formula (c)

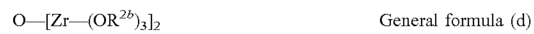

$O—[Zr—(OR^{2b})_3]_2$ General formula (d)

$R^{1b}$ represents a hydrogen atom, an alkyl group, a cycloalkyl group, an acyl group, an aryl group, or an unsaturated aliphatic group.

As the alkyl group, cycloalkyl group, acyl group, aryl group, and unsaturated aliphatic group, for example, the alkyl groups, cycloalkyl groups, acyl groups, aryl groups, and unsaturated aliphatic groups, respectively, that can be employed as $R^{1a}$ in general formula (a) above can be employed.

$R^{2b}$ represents a hydrogen atom, an alkyl group, a cycloalkyl group, an acyl group, an alkenyl group, an aryl group, a phosphonate group, or $—SO_2R^{S2}$. $R^{S2}$ represents a substituent.

As the alkyl group, cycloalkyl group, acyl group, alkenyl group, aryl group, and phosphonate group, for example, the alkyl groups, cycloalkyl groups, acyl groups, alkenyl groups, aryl groups, and phosphonate groups, respectively, that can be employed as $R^{2a}$ in general formula (a) above can be employed. As the substituent that can be employed as $R^{S2}$, for example, the substituents that can be employed as $R^{S1}$ in general formula (a) above can be employed.

m2 is an integer of 0 to 3.

In general formulas (c) and (d) above, at least one of $OR^{2b}$ preferably has an acetonato structure. The acetonato structure has the same meaning as the acetonato structure described in general formula (a). Examples of forms in which $OR^{2b}$ has an acetonato structure include the compounds Z-3 and Z-6 described later.

In general formula (c) above, at least one of $OR^{2b}$ has an acetato structure. The acetato structure has the same meaning as the acetato structure described in general formula (a). An example of a form in which $OR^{2b}$ has an acetato structure is Z-7 described later. The compound Z-5 corresponds to a form in which $R^{2b}$ is an acyl group in general formula (c).

In general formulae (c) and (d) above, at least one of $OR^{2b}$ preferably has a lactato structure. The lactato structure refers to a structure that has a lactate ion (lactate) as a basic structure and that is formed by removing one hydrogen ion from the basic structure and coordinating the resulting structure to Zr. The phrase "have a lactate ion as a basic structure" is meant to include, besides the above lactate ion, a structure obtained by replacing a hydrogen atom of the lactate ion with a substituent. The ligand atom coordinated to Zr is typically an oxygen atom. An example of a form in which $OR^{2b}$ has a lactato structure is the compound Z-4 described later.

Specific examples of the zirconium alkoxide compound used in the present invention are given below; however, the present invention is not limited to these.

Tetrapropoxyzirconium (another name: zirconium tetra-n-propoxide)
Tetrabutoxyzirconium (another name: zirconium tetra-n-butoxide)
Zirconium tetraacetylacetonate
Zirconium tributoxymonoacetylacetonate
Zirconium dibutoxybis(acetylacetonate)
Zirconium dibutoxybis(ethylacetoacetate)
Zirconium tributoxyethylacetoacetate
Zirconium monobutoxyacetylacetonate bis(ethylacetoacetate)

Zirconium tributoxymonostearate (another name: zirconium tri-n-butoxide stearate)
Zirconium stearate
Zirconium lactate ammonium salt
Zirconium monoacetylacetonate
Titanium Alkoxide Compound As the titanium alkoxide compound used in the present invention, typical titanium alkoxide compounds applicable to a primer layer of a flexible tube for an endoscope can be widely employed.

The titanium alkoxide compound preferably includes at least one compound represented by general formula (e) or (f) below, and more preferably includes at least one compound represented by general formula (e) below. The proportion of the total content of the compound represented by the following general formula (e) or (f) in the titanium alkoxide compound is not particularly limited, can be, for example, 60% by mass or more, is preferably 80% by mass or more, more preferably 90% by mass or more, still more preferably 95% by mass or more, and may be 100% by mass.

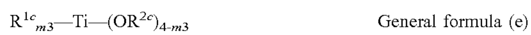

$R^{1c}_{m3}$—Ti—$(OR^{2c})_{4-m3}$ General formula (e)

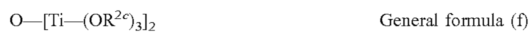

O—[Ti—$(OR^{2c})_3]_2$ General formula (f)

$R^{1c}$ represents a hydrogen atom, an alkyl group, a cycloalkyl group, an acyl group, an aryl group, or an unsaturated aliphatic group.

As the alkyl group, cycloalkyl group, acyl group, aryl group, and unsaturated aliphatic group, for example, the alkyl groups, cycloalkyl groups, acyl groups, aryl groups, and unsaturated aliphatic groups, respectively, that can be employed as $R^{1a}$ in general formula (a) above can be employed.

$R^{2c}$ represents a hydrogen atom, an alkyl group, a cycloalkyl group, an acyl group, an alkenyl group, an aryl group, a phosphonate group, or $—SO_2R^{S3}$. $R^{S3}$ represents a substituent.

As the alkyl group, cycloalkyl group, acyl group, alkenyl group, aryl group, and phosphonate group, for example, the alkyl groups, cycloalkyl groups, acyl groups, alkenyl groups, aryl groups, and phosphonate groups, respectively, that can be employed as $R^{2a}$ in general formula (a) above can be employed. As the substituent that can be employed as $R^{S3}$, for example, the substituents that can be employed as $R^{S1}$ in general formula (a) above can be employed.

m3 is an integer of 0 to 3.

The compound represented by general formula (e) or (f) above preferably includes at least one atom selected from the group consisting of N, P, and S. When the compound represented by general formula (e) or (f) has N, the compound preferably has N in the form of an amino group.

When the compound represented by general formula (e) or (f) has P, the compound preferably has P in the form of a phosphate group (phosphoric acid group) or a phosphonate group (phosphonic acid group).

When the compound represented by general formula (e) or (f) has S, the compound preferably has S in the form of a sulfonyl group ($—SO_2—$).

It is also preferred that the compound represented by general formula (e) or (f) above have an acyl group as $R^{2c}$, that is, the above-described acetato structure as $OR^{2c}$.

Specific examples of the titanium alkoxide compound used in the present invention are given below; however, the present invention is not limited to these.

Isopropyl triisostearoyl titanate
Isopropyl tridodecylbenzenesulfonyl titanate
Isopropyl trioctanoyl titanate
Isopropyl tri(dioctyl phosphite) titanate
Isopropyl tris(dioctylpyrophosphate) titanate
Isopropyl tri(dioctylsulfate) titanate
Isopropyl tricumylphenyl titanate
Isopropyl tri(N-aminoethyl-aminoethyl) titanate
Isopropyl dimethacrylisostearoyl titanate
Isopropyl isostearoyldiacryl titanate
Isobutyl trimethyl titanate
Diisostearoyl ethylene titanate
Diisopropyl bis(dioctylpyrophosphate) titanate
Dioctyl bis(ditridecylphosphate) titanate
Dicumyl phenyloxyacetate titanate
Bis(dioctylpyrophosphate)oxyacetate titanate
Bis(dioctylpyrophosphate)ethylene titanate
Tetraisopropyl titanate
Tetrabutyl titanate
Tetraoctyl titanate
Tetrastearyl titanate
Tetraisopropyl bis(dioctylphosphite) titanate
Tetraoctyl bis(di-tridecylphosphite) titanate
Tetra(2,2-diallyloxymethyl-1-butyl)bis(di-tridecyl)phosphite titanate
Butyl titanate dimer
Titanium tetraacetyl acetonate
Titanium ethylacetoacetate
Titanium octyleneglycolate
Titanium di-2-ethylhexoxy bis(2-ethyl-3-hydroxyhexoxide)

The content of the silane coupling agent and the metal alkoxide compounds in the primer layer is not particularly limited, but is preferably 90% by mass or more, more preferably 95% by mass or more, still more preferably 97% by mass or more, particularly preferably 99% by mass or more, and can be 100% by mass, in total.

Each of the silane coupling agent, the aluminum alkoxide compound, the zirconium alkoxide compound, and the titanium alkoxide compound contained in the primer layer may be one compound or two or more compounds.

The primer layer may contain, in addition to the silane coupling agent and the metal alkoxide compounds, additives such as a surfactant, a thickener, a leveling agent, a stabilizer, and an anti-foaming agent as long as the effects of the present invention are not impaired.

The primer layer may be formed of a single layer or a plurality of layers and is preferably formed of a single layer.

Cover Layer

The flexible tube according to the present invention has a cover layer on an outer periphery of a flexible-tube base having a primer layer thereon.

In the present invention, the cover layer may be formed of a single layer or a multilayer structure including two or more layers and is preferably formed of a single layer. In the present invention, when the cover layer is formed of a single layer, the single-layer cover layer includes a polyester having a naphthalene structure. When the cover layer is formed of a multilayer structure including two or more layers, at least the innermost layer includes a polyester having a naphthalene structure. That is, the cover layer in the present invention includes, in the innermost layer thereof, a polyester having a naphthalene structure.

Polyester having Naphthalene Structure

Examples of the polyester having a naphthalene structure include polyester resins having a naphthalene structure and polyester elastomers having a naphthalene structure.

The polyester having a naphthalene structure is preferably a polyester composed of a dicarboxylic acid component including a naphthalenedicarboxylic acid component and a diol component.

A specific example of the dicarboxylic acid component that is preferred as the naphthalenedicarboxylic acid component is 2,6-naphthalenedicarboxylic acid component.

First, a polyester resin having a naphthalene structure will be described.

The polyester resin having a naphthalene structure preferably has a naphthalenedicarboxylic acid component. The polyester resin having a naphthalenedicarboxylic acid component may have, as the dicarboxylic acid component, a dicarboxylic acid component other than the naphthalenedicarboxylic acid component.

The dicarboxylic acid component other than the naphthalenedicarboxylic acid component is not particularly limited, and those typically used as a dicarboxylic acid component constituting a polyester resin can be widely applied. Examples thereof include constituent components derived from terephthalic acid, isophthalic acid, phthalic acid (orthophthalic acid), 5-sodium sulfoisophthalic acid, oxalic acid, succinic acid, adipic acid, sebacic acid, azelaic acid, dodecanedioic acid, dimer acid, maleic acid, fumaric acid, itaconic acid, citraconic acid, mesaconic acid, cyclohexanedicarboxylic acid, and the like. One or two or more of these dicarboxylic acid components can be used.

In the polyester resin having a naphthalene structure, diol components typically used as a diol component constituting a polyester resin can be widely applied. Examples thereof include constituent components derived from ethylene glycol, diethylene glycol, 1,3-propanediol, 1,4-butanediol, neopentyl glycol, 1,6-hexanediol, cyclohexane dimethanol, triethylene glycol, bisphenol A, bisphenol S, and the like. One or two or more of these diol components can be used.

The polyester resin having a naphthalene structure may contain a hydroxycarboxylic acid component as a constituent component. Examples of the hydroxycarboxylic acid component include constituent components derived from ε-caprolactone, lactic acid, 4-hydroxybenzoic acid, and the like. One or two or more of these hydroxycarboxylic acid components are used.

The polyester resin having a naphthalene structure may be a homopolymer or copolymer composed of the above-described components and may further contain a small amount of a trifunctional compound component such as trimellitic acid, trimesic acid, pyromellitic acid, trimethylolpropane, glycerin, or pentaerythritol.

As the polyester resin having a naphthalene structure, two or more homopolymers or copolymers composed of the above components may be used in combination.

Next, a polyester elastomer having a naphthalene structure will be described.

The polyester elastomer having a naphthalene structure preferably has a naphthalenedicarboxylic acid component. More preferably, the polyester elastomer having a naphthalene structure is a copolymer that contains a hard segment composed of a crystalline polyester chain containing, as constituent components, a dicarboxylic acid component including a naphthalenedicarboxylic acid component and a low-molecular-weight diol component and at least one soft segment selected from the group consisting of (i) to (iii) below.

(i) A soft segment composed of an aliphatic polyester chain (ii) A soft segment composed of an aliphatic polymer diol component (iii) A soft segment composed of a polyester chain containing an aliphatic polymer diol component and a dicarboxylic acid component including an aromatic dicarboxylic acid That is, the naphthalene structure may be introduced in either one or both of the hard segment and the soft segment and is preferably introduced in at least the hard segment.

A specific example of the dicarboxylic acid component that is preferred as the naphthalenedicarboxylic acid component is 2,6-naphthalenedicarboxylic acid component. A polyester elastomer containing a hard segment having a naphthalene structure will be described below.

In the polyester elastomer containing a hard segment having a naphthalene structure, the hard segment preferably has a naphthalenedicarboxylic acid component. When the hard segment has a naphthalenedicarboxylic acid component, all of the dicarboxylic acid components of the hard segment may be the naphthalenedicarboxylic acid component, or the hard segment may have a dicarboxylic acid component other than the naphthalenedicarboxylic acid component. As the dicarboxylic acid component that is other than the naphthalenedicarboxylic acid component and that constitutes the hard segment, those typically used as a dicarboxylic acid component constituting a hard segment of a typical polyester elastomer can be widely applied. Examples thereof include the dicarboxylic acid components that are other than the naphthalenedicarboxylic acid component and described in the description of the polyester resin having a naphthalene structure. The hard segment can have one or two or more of the dicarboxylic acid components. In particular, the dicarboxylic acid component that is other than the naphthalenedicarboxylic acid component and that constitutes the hard segment preferably includes an aromatic dicarboxylic acid component (dicarboxylic acid component having an aromatic ring). The aromatic dicarboxylic acid component preferably accounts for 50% by mass or more (preferably 70% by mass or more, more preferably 80% by mass or more, and more preferably 90% by mass or more) of the dicarboxylic acid component other than the naphthalenedicarboxylic acid component. It is also preferred that all of the dicarboxylic acid components that are other than the naphthalenedicarboxylic acid component and that constitute the hard segment be aromatic dicarboxylic acid components.

As the diol component constituting the hard segment, those typically used as a diol component constituting a polyester resin can be widely applied. Examples thereof include the diol components described in the polyester resin having a naphthalene structure. The hard segment can have one or two or more of the diol components.

The hard segment may have, as a constituent component, one or two or more of the hydroxycarboxylic acid components described in the description of the polyester resin having a naphthalene structure.

The hard segment may be a homopolymer or copolymer composed of the constituent components described above.

When the soft segment is the (i) aliphatic polyester chain, the dicarboxylic acid component constituting the aliphatic polyester chain is not particularly limited as long as the dicarboxylic acid component is an aliphatic dicarboxylic acid component. The aliphatic polyester chain can have a constituent component derived from, for example, oxalic acid, succinic acid, adipic acid, sebacic acid, azelaic acid, dodecanedioic acid, dimer acid, maleic acid, fumaric acid, itaconic acid, citraconic acid, mesaconic acid, cyclohexanedicarboxylic acid, or the like. The aliphatic polyester chain can have one or two or more of these dicarboxylic acid components.

The diol component of the aliphatic polyester chain constituting the soft segment is not particularly limited as long the diol component is an aliphatic diol component. Examples thereof include aliphatic diol components derived from ethylene glycol, diethylene glycol, triethylene glycol, propylene glycol, dipropylene glycol, 3-methyl-1,5-pentanediol, 1,3-propanediol, 1,4-butanediol, 1,9-nonanediol, neopentyl glycol, 1,5-pentanediol, 1,6-hexanediol, decamethylene glycol, cyclohexane dimethanol, and the like. The aliphatic polyester chain can have one or two or more of these diol components. It is also preferred that the aliphatic polyester chain have an aliphatic polymer diol component as the diol component. Examples of the aliphatic polymer diol component include polyalkylene glycols such as polyethylene glycol, polypropylene glycol, and polytetramethylene ether glycol. The aliphatic polyester chain can have one or two or more of these aliphatic polymer diol components. In the present invention, the polyalkylene glycols refer to compounds represented by $HO—[(CH_2)_mO]_n—H$. Here, m is preferably 1 to 12, more preferably 2 to 10, still more preferably 2 to 8, and even more preferably 2 to 6. n is preferably 5 to 100, and more preferably 10 to 50.

When the soft segment is the (ii) amorphous soft segment derived from an aliphatic polymer diol, the aliphatic polymer diol is not particularly limited as long as it is an aliphatic polymer diol. Examples thereof include polyalkylene glycols such as polyethylene glycol, polypropylene glycol, and polytetramethylene ether glycol. The polyester elastomer can have a structure having, as the soft segment, an aliphatic polymer diol component derived from one or two or more of these. The structures of the polyalkylene glycols are as described above.

When the soft segment is the (iii) soft segment composed of a polyester chain containing an aliphatic polymer diol component and a dicarboxylic acid component including an aromatic dicarboxylic acid, the aliphatic polymer diol component is not particularly limited, and examples thereof include constituent components derived from the aliphatic polymer diols described in (ii) above. Examples of the aromatic dicarboxylic acid component include constituent components derived from naphthalenedicarboxylic acids. When the polyester chain includes a dicarboxylic acid component other than the aromatic dicarboxylic acid component, examples of the dicarboxylic acid component include the dicarboxylic acid components described in (i) above.

Examples of the polyesters having a naphthalene structure that are commercially available include TQB-KET30 (manufactured by Teijin Chemicals Ltd.) and PELPRENE EN type (manufactured by Toyobo Co., Ltd.).

The polyesters having a naphthalene structure may be used alone or in combination of two or more thereof.

The content of the polyester having a naphthalene structure in the cover layer when the cover layer is formed of a single layer and the content of the polyester having a naphthalene structure in the innermost layer when the cover layer is formed of a plurality of layers are preferably 50% by mass or more, more preferably 60% by mass or more, still more preferably 70% by mass or more, even more preferably 80% by mass or more, and yet still more preferably 90% by mass or more. When the cover layer is formed of a single layer, the cover layer may be a layer composed of a polyester having a naphthalene structure. When the cover layer is formed of a plurality of layers, the innermost layer may be a layer composed of a polyester having a naphthalene structure.

When the cover layer in the case of the cover layer formed of a single layer and the innermost layer in the case of the cover layer formed of a plurality of layers are composed of a blend of a polyester having a naphthalene structure and a polymer other than a polyester having a naphthalene structure, polymers generally used as a covering material that forms a flexible tube for an endoscope can be widely applied to the polymer. Examples of such a polymer include polyesters having no naphthalene structures, polyurethanes, and polyamides.

The cover layer may appropriately contain various common additives as long as the effects of the present invention are not impaired. Examples of the additives include a heat-resistant stabilizer, a mineral filler, an impact resistance-improving agent, a plasticizer, a lubricant, a metal soap, a light-resistant auxiliary agent, and a colorant. The contents of the additives in the cover layer can also be appropriately adjusted. Such additives may be derived from the material of the polyester having a naphthalene structure to be used or can be added separately from the polyester having a naphthalene structure.

When the cover layer is formed of a plurality of layers, a layer other than the innermost layer also preferably includes a polyester having a naphthalene structure.

Each of the polymers that can be used as the cover layer in the present invention preferably has a molecular weight of 10,000 to 1,000,000, more preferably has a molecular weight of 20,000 to 500,000, and still more preferably has a molecular weight of 50,000 to 300,000.

In the present invention, the molecular weight of the polymer constituting the cover layer means a weight-average molecular weight unless otherwise specified. The weight-average molecular weight can be measured by gel permeation chromatography (GPC) as a molecular weight in terms of polystyrene. Specific measurement conditions are described below.

The weight-average molecular weight can be measured by gel permeation chromatography using an HLC-8220 GPC apparatus (trade name, manufactured by Tosoh Corporation) with chloroform as an eluant and G3000HXL+G2000HXL (each of which is a trade name, manufactured by Tosoh Corporation) as columns at 23° C. and a flow rate of 1 mL/min, while detection is performed with a refractive index (RI) detector.

In the specification of this application, the number-average molecular weight can be measured under the same conditions as those for the weight-average molecular weight. In the specification of this application, when a numerical range of the weight-average molecular weight of a compound is described, the numerical range is also preferred as a numerical range of the number-average molecular weight of the compound.

In the flexible tube according to the present invention, since the flexible-tube base and the cover layer are brought into close contact with each other with the primer layer therebetween, adhesiveness between the flexible-tube base and the cover layer covering the flexible-tube base can be sufficiently maintained even when a bending movement is repeated, and a decrease in adhesiveness between the flexible-tube base and the cover layer is unlikely to occur even when strong sterilization treatment with ozone water is performed. Although the reasons for this are not clear, the reasons are considered as follows.

Presumably, the polyester having a naphthalene structure has a high affinity with a specific silane coupling agent or a metal alkoxide compound and thus can be strongly bound to the flexible-tube base with the primer layer therebetween. In addition, the polyester having a naphthalene structure can have an arrangement in which peeling is unlikely to occur against a bending movement due to the planar structure of a naphthalene ring, the arrangement being characteristic of a molecule having a naphthalene structure.

Furthermore, the naphthalene structure is considered to have a barrier property of inhibiting migration and permeation of active species that exhibit a sterilizing function, such as hydroxy radicals, in the cover layer because of its large molecular area. When a polyester having such a structure is joined to the flexible-tube base with a metal alkoxide compound or the like therebetween, not only the binding between the cover layer and the flexible-tube base is enhanced to a high level, but also the naphthalene structure can be arranged in the cover layer at a position where migration and permeation of the active species can be effectively inhibited, while, for example, the π-π interaction also acts as a factor in some cases.

Topcoat Layer

In the flexible tube according to the present invention, a topcoat layer (not illustrated) is disposed on an outer periphery of a cover layer 15 as needed. The material of the top coat layer is not particularly limited, but a urethane coating, an acrylic coating, a fluorine coating, a silicone coating, an epoxy coating, a polyester coating, or the like is applied.

Main purposes of use of the topcoat layer are to protect the surface of the flexible tube or make the surface glossy, to impart slidability, and to impart chemical resistance. Therefore, the topcoat layer preferably has a high modulus of elasticity, a smooth surface, and good chemical resistance.

Method for Producing Flexible Tube

Formation of Primer Layer

In the production of a flexible tube according to the present invention, first, a primer layer is formed on an outer periphery of a flexible-tube base. The primer layer can be formed by dissolving at least one of a silane coupling agent, an aluminum alkoxide compound, a zirconium alkoxide compound, or a titanium alkoxide compound in a solvent to prepare a coating liquid; forming a coating film on at least the outer periphery of the flexible-tube base by, for example, applying or spraying the coating liquid to the outer periphery of the flexible-tube base or immersing the flexible-tube base into the coating liquid; and subsequently drying the coating film by an ordinary method (for example, high-temperature drying at 100° C. to 170° C.).

Examples of the solvent that can be used for the coating liquid include alcohol solvents such as methanol and ethanol; ketone solvents such as acetone and methyl ethyl ketone; ester solvents such as ethyl acetate; hydrocarbon solvents such as toluene; and liquid mixtures thereof. It is preferable to mix water with the solvents in order to accelerate hydrolysis of an alkoxy group of at least one of the aluminum alkoxide compound, the zirconium alkoxide compound, or the titanium alkoxide compound. The same applies to a case where the silane coupling agent has an alkoxy group. The pH of the coating liquid is not particularly limited, but may be adjusted as required to be acidic (for example, pH 1 to 4 at 25° C.) or alkaline (for example, pH 9 to 11 at 25° C.) by using a pH adjuster, for example.

The content of at least one of the silane coupling agent, the aluminum alkoxide compound, the zirconium alkoxide compound, or the titanium alkoxide compound in the coating liquid is not particularly limited, can be, for example, 0.01% by mass to 2% by mass, and is preferably 0.05% by mass or more and less than 1.5% by mass, and more preferably 0.1% by mass or more and less than 1.0% by mass.

The coating liquid may include, for example, a surfactant and a catalyst besides at least one of the silane coupling agent, the aluminum alkoxide compound, the zirconium alkoxide compound, or the titanium alkoxide compound, the solvent, and the pH adjuster. The coating liquid is more preferably constituted by at least one of the silane coupling agent, the aluminum alkoxide compound, the zirconium alkoxide compound, or the titanium alkoxide compound and the solvent.

In the present invention, a portion that is not covered with the primer layer may be present on the outer periphery of the flexible-tube base as long as the effects of the present invention are not impaired (that is, the primer layer may have a defect in a portion thereof).

Prior to the formation of the primer layer, the flexible-tube base is preferably cleaned by degreasing with an alkali solution, an aqueous solution of a surfactant, an organic solvent, or the like. After the cleaning, the flexible-tube base is preferably further washed with water or hot water. After the washing with water or hot water, drying is preferably performed (for example, at 100° C. for 10 minutes).

Formation of Cover Layer

The production of the flexible tube for an endoscope according to the present invention includes a step of forming a cover layer. The step of forming a cover layer includes forming, on a primer layer formed on an outer periphery of the flexible-tube base (so as to be in contact with the primer layer), a cover layer using a cover layer-forming material that includes a polyester having a naphthalene structure. The formation itself of the cover layer using the cover layer-forming material can be performed by an ordinary method. For example, the cover layer can be formed by subjecting the cover layer-forming material to extrusion coating (forming temperature: 150° C. to 250° C.). When the cover layer-forming material contains a component other than the polyester having a naphthalene structure, the cover layer can be formed by, for example, kneading the components used for the cover layer-forming material with a twin-screw kneader and subjecting the resulting mixture to extrusion coating.

Endoscopic Medical Device

The flexible tube according to the present invention is widely applicable to endoscopic medical devices. For example, the flexible tube according to the present invention is applicable to an endoscope equipped with a clip or wire at the distal end thereof or to a device equipped with a basket or brush. Note that the term "endoscopic medical device" is meant to broadly include, besides medical devices that include an endoscope as a basic structure, medical devices and diagnosis and treatment devices that include an insertion section having flexibility and that are introduced and used in the inside of the body, such as remote-controlled medical devices.

An endoscopic medical device according to the present invention has an insertion section in which the flexible tube for an endoscope according to the present invention is incorporated. That is, a method for producing an endoscopic medical device according to the present invention includes incorporating, into an insertion section of an endoscopic medical device, a flexible tube for an endoscope according to the present invention or a flexible tube for an endoscope, the flexible tube being obtained by the method for producing a flexible tube for an endoscope according to the present invention.

An electronic endoscope will now be described as an example of an endoscopic medical device according to a preferred embodiment of the present invention. An electronic endoscope includes a flexible tube for an endoscope, the flexible tube being incorporated therein, and is used as a medical device for, for example, examining the inside of the body cavity by inserting the flexible tube into the inside of the body cavity. In an example illustrated in FIG. 1, an electronic endoscope 2 includes an insertion section 3 to be inserted into the body cavity, a main-body operation section 5 connected to a proximal end portion of the insertion section 3, and a universal cord 6 to be connected to a processor device or a light source device. The insertion section 3 is constituted by a flexible tube 3*a* connected to the main-body operation section 5, an angle portion 3*b* connected to the flexible tube 3*a*, and a tip portion 3*c* connected to the distal end of the angle portion 3*b* and including therein an imaging device (not illustrated) for capturing an image of the inside of the body cavity. The flexible tube 3*a*, which accounts for most of the length of the insertion section 3, has flexibility across substantially the entire length thereof and is configured so that, in particular, a portion to be inserted into the inside of the body cavity or the like has higher flexibility.

Flexible Tube

The flexible tube has, as an innermost layer, a flexible-tube base containing metal as a constituent material.

Figure 2:
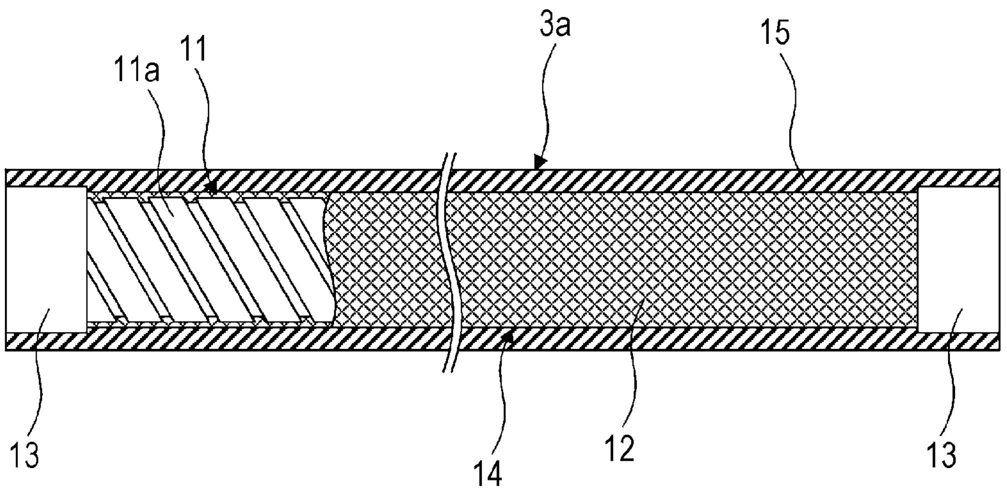
FIG. 2 is a partial sectional view illustrating a schematic configuration of a flexible tube for an endoscope.

As illustrated in FIG. 2, a flexible-tube base 14 preferably has a form in which a spiral tube 11 disposed on the innermost side and formed by spirally winding a metal strip 11*a* is covered with a tubular mesh 12 formed by weaving metal wires, and caps 13 are fitted to both ends of the flexible-tube base 14. The metal constituting the flexible-tube base 14 preferably has a surface that has been subjected to passivation treatment in order to prevent corrosion. That is, the flexible-tube base 14 preferably has a passivation film on an outer periphery thereof. This passivation treatment can be performed by an ordinary method. A passivation film can be formed on a surface of metal by, for example, immersing the metal in a solution including a strong oxidizing agent such as nitric acid, heating the metal in air (oxygen) or water (water vapor), or anodizing the metal in a solution including an oxidizing agent.

The metal that constitutes the flexible-tube base 14 is preferably stainless steel. The surface of stainless steel is usually in a state in which chromium and oxygen are bound together to form a passivation film. However, even when stainless steel is used as the constituent material of the flexible-tube base 14, the stainless steel is preferably subjected to the passivation treatment described above in order to more reliably form a more uniform passivation film over the entire surface of the stainless steel.

In this embodiment, the cover layer 15 is formed with a substantially uniform thickness in the longitudinal direction (axial direction) of the flexible-tube base 14. The cover layer 15 has a thickness of, for example, 0.1 to 0.6 mm, and the flexible tube 3*a* has an outer diameter D of, for example, 1.7 to 13.5 mm, preferably 3.0 to 8.0 mm. Furthermore, the flexible-tube base 14 has an outer diameter of, for example, 1.6 to 12.5 mm, preferably 2.2 to 7.8 mm. When the flexible tube according to the present invention is used for insertion into the bronchus, the thickness of the cover layer 15 is preferably 0.1 to 0.3 mm, the outer diameter D of the flexible tube 3*a* is preferably 3.0 to 5.0 mm, and the outer diameter of the flexible-tube base 14 is preferably 2.4 to 4.8 mm.

EXAMPLES

Hereafter, the present invention will be described in more detail by way of Examples. However, these Examples should not be construed as limiting the present invention.

Preparation of Cover Layer-Forming Material

For Examples 1 to 28 and 32, a polyester having a naphthalene structure (R) shown in Tables 1-1 to 1-3 below (hereinafter, at least one of Tables 1-1 to 1-3 is referred to as Table 1) was used.

For Examples 29 to 31, samples each prepared as described below were used.

A composition prepared by blending the polyester having a naphthalene structure (R) and another polymer (Q) shown in Table 1 below at a ratio shown in Table 1 below was introduced into a twin-screw kneader (manufactured by Technovel Corporation, KZW15-30MG, trade name) in which a barrel temperature and a die temperature were set to 220° C., and kneaded at a screw rotation speed of 100 rpm. A strand in a molten state discharged from the twin-screw kneader was cooled in a water tank and then cut with a pelletizer to obtain a pellet-shaped sample.

Preparation of Flexible-Tube Base

Flexible-tube bases used in Examples and Comparative Examples will be descried with reference to FIG. 2.

Each of the flexible-tube bases prepared had a form in which a spiral tube 11 was formed by using a metal strip 11*a* made of stainless steel, and the spiral tube 11 was covered with a tubular mesh 12 formed by weaving stainless steel fibers. The flexible-tube base has a length of 80 cm and a diameter of 12 mm. The stainless steel flexible-tube base has a passivation layer on a surface thereof, the passivation layer being formed by annealing treatment (heating treatment) at the time of the formation of the spiral tube and the tubular mesh.

Preparation of Primer Layer-Forming Coating Liquid

In a solution prepared by mixing water and ethanol at a mass ratio of 5:75, a primer layer-forming component shown in Table 1 below was dissolved so as to have a concentration of 8.9 g/kg. The resulting solution was used as a primer layer-forming coating liquid.

Formation of Primer Layer

The above flexible-tube base was cleaned by immersing in a 7.5% aqueous sodium hydroxide solution at 60° C. for one minute and then rinsed with distilled water. The flexible-tube base was dried in an oven at 100° C. for 10 minutes, then immersed in the above-prepared primer layer-forming coating liquid at room temperature for one minute, and then dried in an oven at 160° C. for 10 minutes. Thus, a flexible-tube base having a primer layer on the outer periphery and the inner periphery thereof was prepared.

Formation of Cover Layer

The outer periphery of the flexible-tube base having the primer layer thereon was covered with the cover layer-forming material prepared above by extrusion (molding temperature: 220° C.) to produce a flexible tube for an endoscope, the flexible tube having a cover layer. The cover layer had a thickness of 0.4 mm.

Test Example 1 (Peeling Resistance)

The flexible tube for an endoscope produced as described above was subjected to a bending operation.

Specifically, a cylindrical rod was applied to the center of the flexible tube for an endoscope in the length direction (at a position 40 cm from one terminal of the flexible tube in the axial direction), and the flexible tube was bent into a U-shape with a radius of curvature of 5 cm and then returned to a straight state. This movement was defined as one back-and-forth movement, and this movement was performed for 5,000 back-and-forth movements.

For the cover layer of the flexible tube for an endoscope after the bending operation, a slit with a width of 1 cm was made in a direction perpendicular to the axial direction (length direction) at a position 40 cm from one terminal of the flexible tube in the axial direction (center in the length direction) such that the slit reached the flexible-tube base. Slits with a length of 10 cm were made from both terminals of the slit along the axial direction of the flexible tube such that the slits reached the flexible-tube base.

This flexible tube was subjected to a 90° peel test using a peel tester (trade name: FGS-500TV, manufactured by Nidec-Shimpo Corporation). The edges of the slits were grasped, and the cover layer was peeled off at a constant rate of 2 mm/minute in the axial direction to measure a peel strength (measured value X1 (N/cm)). The peel strength was measured with a force gauge.

For a flexible tube for an endoscope, the flexible tube not having been subjected to the bending operation described above, the 90° peel test was also performed to measure a peel strength (measured value Y1 (N/cm)). The value (%) obtained from formula 1) below was evaluated on the basis of the following scale. "C" or higher is satisfactory.

$$100\times X1/Y1\ (\%) \quad \text{Formula 1}$$

Evaluation Scale

AA: 80% or more

A: 60% or more and less than 80%

B: 40% or more and less than 60%

C: 20% or more and less than 40%

D: less than 20% (including a completely peeled state)

Test Example 2 (Sterilization Durability)

The flexible tube for an endoscope produced as described above was subjected to ozone water treatment.

Specifically, the flexible tube for an endoscope was placed in a flow path of an ozone water generating device ("OWM-10L1OP" (trade name) manufactured by EcoDesign, Inc.), and ozone water having an ozone concentration of 3 ppm was caused to flow at a flow rate of 1 L/min for three hours to perform treatment.

The flexible tube for an endoscope after the ozone water treatment was subjected to the bending operation described above, and for the flexible tube for an endoscope after the bending operation, slits were made in the same manner as described above, and the peel strength was measured (measured value X2 (N/cm)). The value (%) obtained from formula 2) below was evaluated on the basis of the following scale. "C" or higher is satisfactory.

$$100\times X2/Y1\ (\%) \quad \text{Formula 2}$$

(In formula 2), Y1 has the same meaning as Y1 in formula 1)).

Evaluation Scale

A: 80% or more

B: 60% or more and less than 80%

C: 40% or more and less than 60%

D: less than 40% (including a state where peeling occurred during treatment)

TABLE 1

| | | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|---|
| Cover layer-forming component (parts by mass) | Polyester having naphthalene structure (R) | (R-1) 100 | (R-1) 100 | (R-1) 100 | (R-1) 100 | (R-1) 100 | (R-1) 100 | (R-1) 100 | (R-1) 100 | (R-1) 100 | (R-1) 100 |
| | Other polymer (Q) | | | | | | | | | | |
| Primer layer-forming component | Silane coupling agent (S) | (S-1) | (S-2) | (S-3) | (S-4) | (S-5) | (S-6) | | | | |
| | Titanium alkoxide compound (T) | | | | | | | | | | |
| | Aluminum alkoxide compound (A) | | | | | | | (A-1) | (A-2) | (A-3) | (A-4) |
| | Zirconium alkoxide compound (Z) | | | | | | | | | | |
| Evaluation results | Test Example 1 (Peeling resistance) | C | B | A | B | A | A | B | A | A | A |
| | Test Example 2 (Sterilization durability) | C | C | C | A | B | C | B | A | A | A |

| | | Ex. 11 | Ex. 12 | Ex. 13 | Ex. 14 | Ex. 15 | Ex. 16 | Ex. 17 | Ex. 18 | Ex. 19 | Ex. 20 |
|---|---|---|---|---|---|---|---|---|---|---|---|
| Cover layer-forming component (parts by mass) | Polyester having naphthalene structure (R) | (R-1) 100 | (R-1) 100 | (R-1) 100 | (R-1) 100 | (R-1) 100 | (R-1) 100 | (R-1) 100 | (R-1) 100 | (R-1) 100 | (R-1) 100 |
| | Other polymer (Q) | | | | | | | | | | |
| Primer layer-forming component | Silane coupling agent (S) | | | | | | | | | | |
| | Titanium alkoxide compound (T) | | | | | | | | | (T-1) | (T-2) |
| | Aluminum alkoxide compound (A) | (A-5) | | | | | | | | | |
| | Zirconium alkoxide compound (Z) | | (Z-1) | (Z-2) | (Z-3) | (Z-4) | (Z-5) | (Z-6) | (Z-7) | | |
| Evaluation results | Test Example 1 (Peeling resistance) | A | C | C | A | A | B | B | B | B | B |
| | Test Example 2 (Sterilization durability) | A | B | B | A | A | B | A | A | A | A |

TABLE 1-continued

| | | Ex. 21 | Ex. 22 | Ex. 23 | Ex. 24 | Ex. 25 | Ex. 26 | Ex. 27 | Ex. 28 | Ex. 29 | Ex. 30 | Ex. 31 | Ex. 32 |
|---|---|---|---|---|---|---|---|---|---|---|---|---|---|
| Cover layer-forming component (parts by mass) | Polyester having naphthalene structure (R) | (R-1) 100 | (R-1) 100 | (R-1) 100 | (R-1) 100 | (R-1) 100 | (R-1) 100 | (R-1) 100 | (R-1) 100 | (R-1) 70 | (R-1) 70 | (R-1) 70 | (R-2) 100 |
| | Other polymer (Q) | | | | | | | | | (Q-1) 30 | (Q-2) 30 | (Q-3) 30 | |
| Primer layer-forming component | Silane coupling agent (S) | | | | | | | | | | | | |
| | Titanium alkoxide compound (T) | (T-3) | (T-4) | (T-5) | (T-6) | (T-7) | (T-8) | (T-9) | (T-10) | (T-4) | (T-4) | (T-4) | (T-4) |
| | Aluminum alkoxide compound (A) | | | | | | | | | | | | |
| | Zirconium alkoxide compound (Z) | | | | | | | | | | | | |
| Evaluation results | Test Example 1 (Peeling resistance) | A | AA | AA | AA | AA | AA | AA | A | A | A | A | AA |
| | Test Example 2 (Sterilization durability) | A | A | A | A | A | A | A | A | A | A | A | A |

| | | Com. 1 | Com. 2 | Com. 3 | Com. 4 | Com. 5 | Com. 6 | Com. 7 | Com. 8 | Com. 9 |
|---|---|---|---|---|---|---|---|---|---|---|
| Cover layer-forming component (parts by mass) | Polyester having naphthalene structure (R) | (R-1) 100 | (R-1) 100 | (R-1) 100 | (R-1) 100 | (R-1) 100 | (R-1) 100 | | | |
| | Other polymer (Q) | | | | | | | (Q-1) 100 | (Q-2) 100 | (Q-3) 100 |
| Primer layer-forming component | Silane coupling agent (S) | | (s-7) | (s-8) | (s-9) | (s-10) | (s-11) | | | |
| | Titanium alkoxide compound (T) | | | | | | | (T-4) | (T-4) | (T-4) |
| | Aluminum alkoxide compound (A) | | | | | | | | | |
| | Zirconium alkoxide compound (Z) | | | | | | | | | |
| Evaluation results | Test Example 1 (Peeling resistance) | D | D | D | C | C | D | D | D | D |
| | Test Example 2 (Sterilization durability) | D | D | D | D | D | D | D | D | D |

Description of Terms in Tables

Ex.: Example

Com.: Comparative Example

Polyester Having Naphthalene Structure (R)

(R-1) Polyester elastomer having polybutylene naphthalate as structural unit (manufactured by Toyobo Co., Ltd., trade name "PELPRENE EN-5000", weight-average molecular weight: 119,000)

(R-2) Polyester elastomer having polybutylene naphthalate as structural unit (manufactured by Toyobo Co., Ltd., trade name "PELPRENE EN-1000", weight-average molecular weight: 131,000)

Other polymer (Q)

(Q-1) Polyester elastomer having polybutylene terephthalate as structural unit (manufactured by Toyobo Co., Ltd., trade name "PELPRENE P-280B", weight-average molecular weight: 128,000)

(Q-2) Ether-based polyurethane elastomer (manufactured by Nippon Polyurethane Industry Co., Ltd., trade name "MIRACTRAN E574PNAT", weight-average molecular weight: 145,000)

(Q-3) Polyamide elastomer (manufactured by Arkema Inc., trade name "Pebax 7233", weight-average molecular weight: 48,000)

Silane Coupling Agent (S)

Compounds used in Examples (S-1): p- Styryltrimethoxysilane (trade name: KBM-1403, manufactured by Shin-Etsu Chemical Co., Ltd.)

(S-2): 3-Ureidopropyltrialkoxysilane (trade name: KBE-585A, manufactured by Shin-Etsu Chemical Co., Ltd.)

(S-3): 3-Isocyanatepropyltriethoxysilane (trade name: KBM-9007N, manufactured by Shin-Etsu Chemical Co., Ltd.)

(S-4): Bis(3-trimethoxysilylpropyl)fumarate (trade name "SIB1834.5", manufactured by Gelest, Inc.)

(S-5): Tris(trimethoxysilylpropyl)isocyanurate (trade name: KBM-9659, manufactured by Shin-Etsu Chemical Co., Ltd.)

(S-6): 3-Trimethoxysilylpropylsuccinic anhydride (trade name: X-12-967C, manufactured by Shin-Etsu Chemical Co., Ltd.)

Compounds Used in Comparative Examples (s-7): Vinyltrimethoxysilane (trade name: KBM-1003, manufactured by Shin-Etsu Chemical Co., Ltd.)

(s-8): (3-Methacryloxypropyl)trimethoxysilane (trade name: KBM-503, manufactured by Shin-Etsu Chemical Co., Ltd.)

(s-9): 3-Glycidoxypropyltrimethoxysilane (trade name: KBM-403, manufactured by Shin-Etsu Chemical Co., Ltd.)

(s-10): 3-Aminopropyltrimethoxysilane (trade name: KBM-903, manufactured by Shin-Etsu Chemical Co., Ltd.)

(s-11): 3-Mercaptopropyltrimethoxysilane (trade name: KBM-803, manufactured by Shin-Etsu Chemical Co., Ltd.)

Titanium Alkoxide Compound (T)

(T-1): Tetra-n-butyl titanate (trade name: ORGATIX TA-21, manufactured by Matsumoto Fine Chemical Co., Ltd.)

T-1

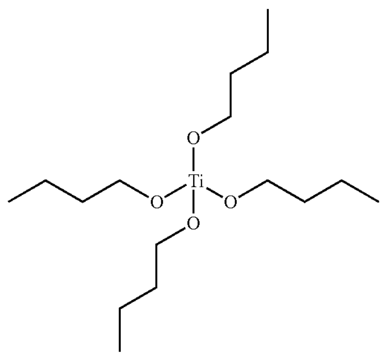

(T-2): n-Butyl titanate dimer (trade name: "ORGATIX TA-23" manufactured by Matsumoto Fine Chemical Co., Ltd.)

T-2

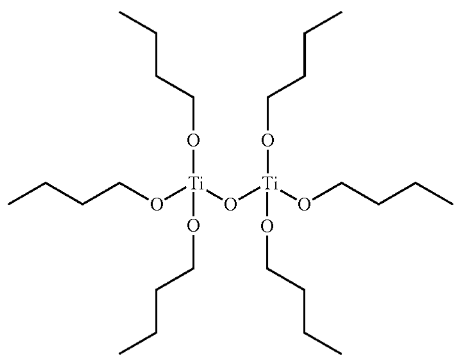

(T-3): Isopropyl triisostearoyl titanate (trade name: "PLENACT TTS" manufactured by Ajinomoto Fine-Techno Co., Inc.)

T-3

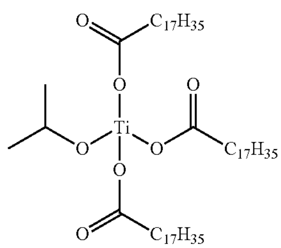

(T-4): Dioctyl bis(ditridecyl phosphate) titanate (trade name: "PLENACT 46B" manufactured by Ajinomoto Fine-Techno Co., Inc.)

T-4

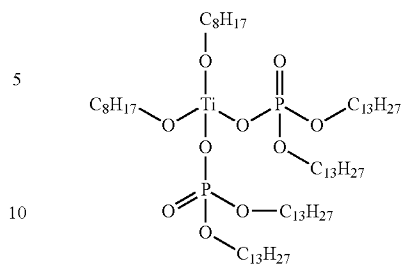

(T-5): Diisopropyl bis(dioctyl pyrophosphate) titanate (trade name: "PLENACT 38S" manufactured by Ajinomoto Fine-Techno Co., Inc.)

T-5

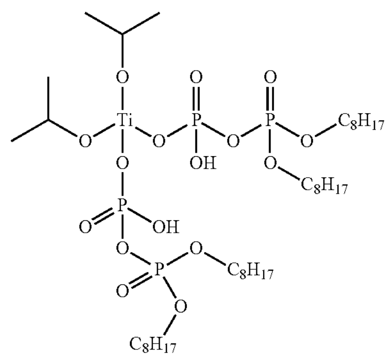

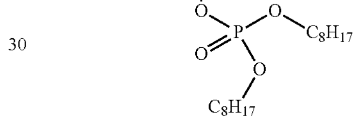

(T-6): Bis(dioctylpyrophosphate)oxyacetate titanate (trade name: "PLENACT 138S" manufactured by Ajinomoto Fine-Techno Co., Inc.)

T-6

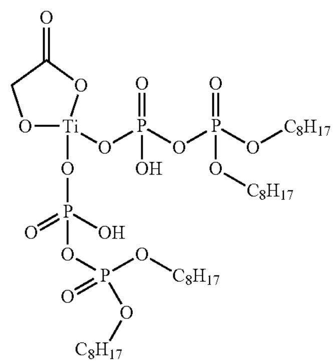

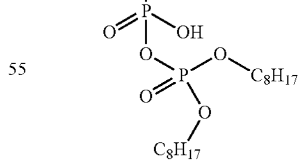

(T-7): Bis(dioctylpyrophosphate)ethylene titanate (trade name: "PLENACT 238S" manufactured by Ajinomoto Fine-Techno Co., Inc.)

T-7

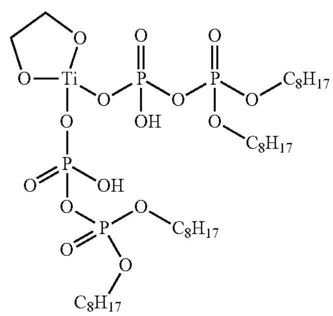

(T-8): Isopropyl tri(N-aminoethyl-aminoethyl) titanate (trade name: "PLENACT 44" manufactured by Ajinomoto Fine-Techno Co., Inc.)

T-8

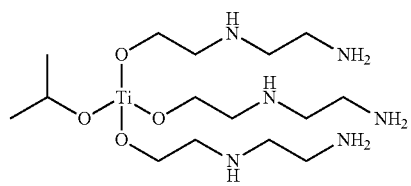

(T-9): Isopropyl tridodecylbenzenesulfonyl titanate (trade name: "PLENACT 9SA" manufactured by Ajinomoto Fine-Techno Co., Inc.)

T-9

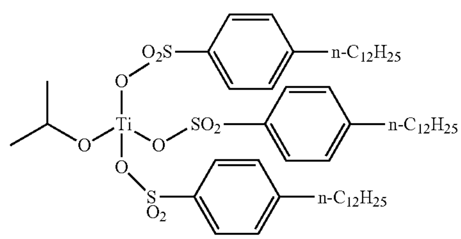

(T-10): Titanium di-2-ethylhexoxybis(2-ethyl-3-hydroxyhexoxide) (trade name: "ORGATIX TC-201" manufactured by Matsumoto Fine Chemical Co., Ltd.)

T-10

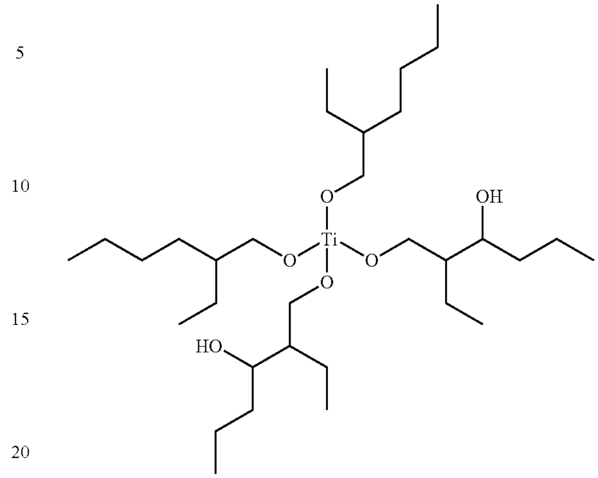

Aluminum Alkoxide Compound (A)

(A-1): Aluminum sec-butoxide (trade name: "ASBD" manufactured by Kawaken Fine Chemicals Co., Ltd.)

A-1

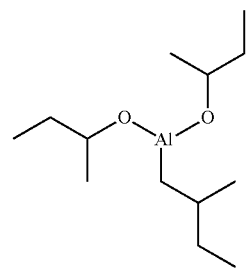

(A-2): Aluminum trisacetylacetonate (trade name: "ORGATIX AL-3100" manufactured by Matsumoto Fine Chemical Co., Ltd.)

A-2

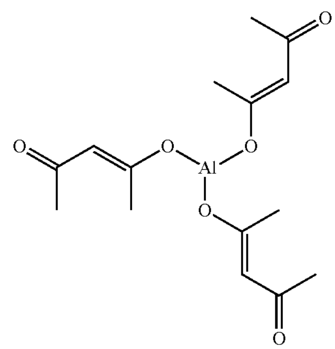

(A-3): Aluminum bisethylacetoacetate monoacetylacetonate (trade name: "ORGATIX AL-3200" manufactured by Matsumoto Fine Chemical Co., Ltd.)

A-3

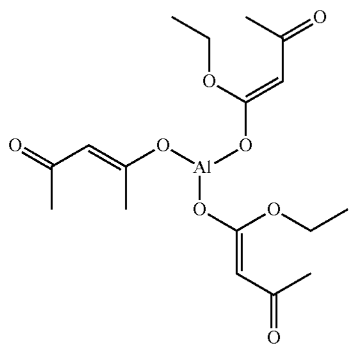

(A-4): Aluminum trisethylacetoacetate (trade name: “ORGATIX AL-3215” manufactured by Matsumoto Fine Chemical Co., Ltd.)

A-4

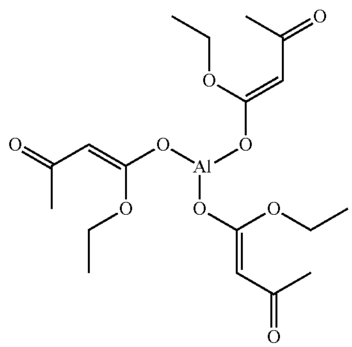

(A-5): Aluminum octadecylacetoacetate diisopropylate (trade name: “PLENACT AL-M” manufactured by Ajinomoto Fine-Techno Co., Inc.)

A-5

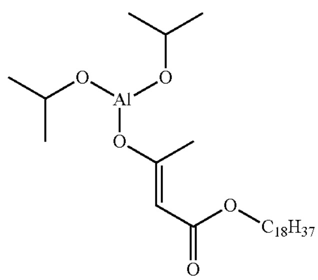

Zirconium Alkoxide Compound (Z)

(Z-1): Zirconium tetra-n-propoxide (trade name: “ORGATIX ZA-45” manufactured by Matsumoto Fine Chemical Co., Ltd.)

Z-1

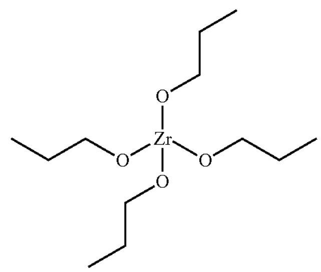

(Z-2): Zirconium tetra-n-butoxide (trade name: “ORGATIX ZA-65” manufactured by Matsumoto Fine Chemical Co., Ltd.)

z-2

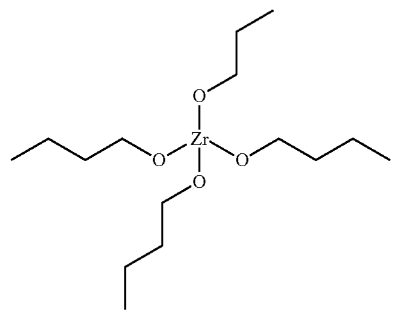

(Z-3): Zirconium tetraacetylacetonate (trade name: “ORGATIX ZC-150” manufactured by Matsumoto Fine Chemical Co., Ltd.)

Z-3

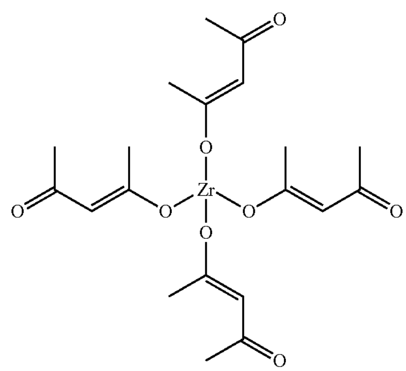

(Z-4): Zirconium lactate ammonium salt (trade name: “ORGATIX ZC-300” manufactured by Matsumoto Fine Chemical Co., Ltd.)

Z-4

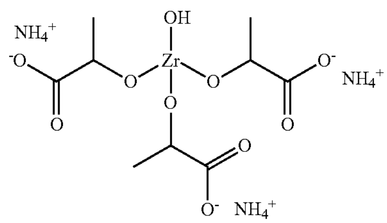

(Z-5): Zirconium tri-n-butoxide stearate (trade name: "ORGATIX ZC-320" manufactured by Matsumoto Fine Chemical Co., Ltd.)

Z-5

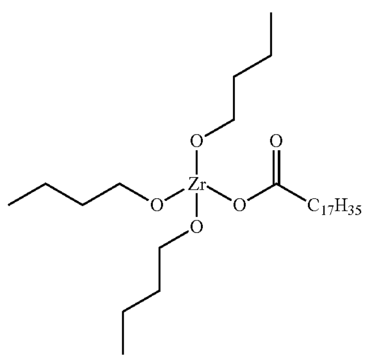

(Z-6): Zirconium tri-n-butoxymonoacetylacetonate (trade name: "ORGATIX ZC-540" manufactured by Matsumoto Fine Chemical Co., Ltd.)

Z-6

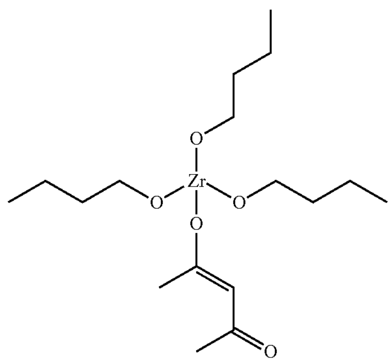

(Z-7): Zirconium di-n-butoxybis(ethylacetoacetate) (trade name: "ORGATIX ZC -580" manufactured by Matsumoto Fine Chemical Co., Ltd.)

Z-7

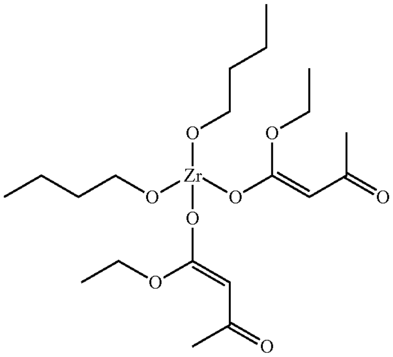

As is clear from Table 1, in Comparative Example 1, since neither the silane coupling agent nor the metal alkoxide compounds specified in the present invention was used, the peeling resistance and the sterilization durability were unsatisfactory.

In Comparative Examples 2 to 6, since silane coupling agents that did not satisfy the conditions specified in the present invention were used, at least the sterilization durability was unsatisfactory. Probably, this is because each of the silane coupling agents that do not satisfy the conditions specified in the present invention has low sterilization durability, or the bond between the silane coupling agent and at least one of the flexible-tube base or the cover layer is easily broken.

The results of Comparative Examples 7 to 9 show that even when a metal alkoxide compound specified in the present invention is used, the peeling resistance and the sterilization durability are unsatisfactory unless a polyester having a naphthalene structure is used in the cover layer.

On the other hand, in Examples 1 to 32 of the present invention, the peeling resistance and the sterilization durability were all satisfactory. In particular, the results of Examples 7 to 32 show that the sterilization durability can be increased to a higher level (all evaluated as "B" or higher) by using the metal alkoxide compounds specified in the present invention in the primer layer.

The present invention has been described together with embodiments thereof; however, we do not intend to limit our invention in any of the details of the description unless otherwise specified. We believe that the invention should be broadly construed without departing from the spirit and scope of the invention as defined by the appended claims.

REFERENCE SIGNS LIST

2 electronic endoscope (endoscope)
3 insertion section
3*a* flexible tube
3*b* angle portion
3*c* tip portion
5 main-body operation section
6 universal cord
11 spiral tube
11*a* metal strip
12 tubular mesh
13 cap
14 flexible-tube base
15 cover layer

What is claimed is:

1. A flexible tube for an endoscope, the flexible tube comprising:

a flexible-tube base containing metal as a constituent material;

a cover layer covering an outer periphery of the flexible-tube base; and a primer layer disposed between the flexible-tube base and the cover layer and including at least one of a silane coupling agent, an aluminum alkoxide compound, a zirconium alkoxide compound, or a titanium alkoxide compound, wherein the cover layer includes, at least on a side in contact with the primer layer, a polyester having a naphthalene structure, provided that the silane coupling agent includes none of a vinyl silane coupling agent, a (meth)acrylic silane coupling agent, an epoxy silane coupling agent, an amino silane coupling agent, and a sulfanyl silane coupling agent.

2. The flexible tube for an endoscope according to claim 1, wherein the metal that constitutes the flexible-tube base is stainless steel.

3. The flexible tube for an endoscope according to claim 1, wherein the metal that constitutes the flexible-tube base has a passivation film on a surface of the metal.

4. An endoscopic medical device comprising the flexible tube for an endoscope according to claim 1.

5. The flexible tube for an endoscope according to claim 1, wherein the silane coupling agent excludes a compound represented by general formula (A) below:

General formula (A)

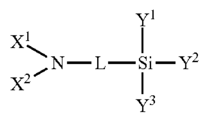

in the formula (A), $X^1$ and $X^2$ each represent a hydrogen atom, an alkyl group, a cycloalkyl group, an alkenyl group, an aryl group, an acyl group, an alkoxycarbonyl group, or a carbamoyl group, $Y^1$ represents a hydroxy group or an alkoxy group, $Y^2$ and $Y^3$ each represent a hydroxy group, an alkoxy group, or an alkyl group, L represents a single bond, or a divalent group selected from an alkylene group, an arylene group, and —O—, or a divalent group formed by combining two or more divalent groups thereof.

6. The flexible tube for an endoscope according to claim 1, wherein the polyester elastomer having a naphthalene structure is a copolymer that contains a hard segment composed of a crystalline polyester chain containing, as constituent components, a dicarboxylic acid component including a naphthalenedicarboxylic acid component and a low-molecular-weight diol component and at least one soft segment selected from the group consisting of (i) to (iii) below:

(i) a soft segment composed of an aliphatic polyester chain, (ii) a soft segment composed of an aliphatic polymer diol component, and (iii) a soft segment composed of a polyester chain containing an aliphatic polymer diol component and a dicarboxylic acid component including an aromatic dicarboxylic acid.

7. The flexible tube for an endoscope according to claim 1, wherein the silane coupling agent includes a compound represented by general formula (1) below:

General formula (1)

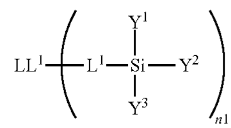

where $LL^1$ represents a monovalent substituent or an n1-valent linking group, $L^1$ represents a single bond or a divalent linking group, $Y^1$ to $Y^3$ each represent a substituent, and n1 is an integer of 1 to 4, provided that at least one of $Y^1$ to $Y^3$ is a group selected from the group consisting of alkoxy groups and a hydroxy group, and when n1 is 1, $LL^1$, $LL^1$-$L^1$, and $Y^1$ to $Y^3$ do not simultaneously represent groups selected from the group consisting of alkoxy groups and a hydroxy group, and the compound represented by general formula (1) includes none of a vinyl silane coupling agent, a (meth)acrylic silane coupling agent, an epoxy silane coupling agent, an amino silane coupling agent, and a sulfanyl silane coupling agent.

8. The flexible tube for an endoscope according to claim 7, wherein the compound represented by general formula (1) includes a compound represented by any of general formulae (2) to (4) below:

General formula (2)

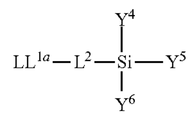

General formula (3)

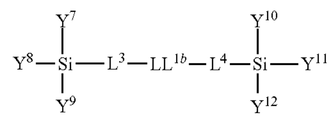

General formula (4)

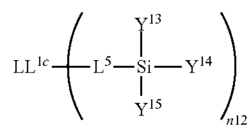

where $LL^{1a}$ represents a hydrogen atom, an alicyclic group, a heterocyclic group, a hydroxy group, a sulfanyl group, an isocyanato group, a thiocyanato group, a ureido group, a cyano group, an acid anhydride group, an azide group, a carboxy group, an acyl group, a thiocarbamoyl group, a phosphoric acid group, a phosphanyl group, a sulfonic acid group, or a sulfamoyl group, $L^2$ represents a single bond, an alkylene group, an alkenylene group, an alkynylene group, an arylene group, —O—, —S—, —$NR^a$—, an ester bond, a thioester bond, an amide bond, a thioamide bond, a sulfonyl group, or a divalent group formed by combining two or more selected from the group consisting of the aforementioned groups and bonds, $L^3$ to $L^5$ each represent a single bond, an alkylene group, an alkenylene group, an alkynylene group, an arylene group, —O—, —S—, —$NR^a$—, an ester bond, a thioester bond, an amide bond, a thioamide bond, a urea bond, a thiourea bond, a sulfonyl group, or a divalent group formed by combining two or more selected from the group consisting of the aforementioned groups and bonds, $LL^{1b}$ represents a single bond, an alkylene group, an alkenylene group, an alkynylene group, an arylene group, —O—, —S—, —$NR^a$—, a divalent heterocyclic group, an amide bond, an ester bond, a thioester bond, a divalent phosphoric acid group, a phosphanediyl group, a sulfonyl group, or a divalent group formed by combining two or more selected from the group consisting of the aforementioned groups and bonds, $LL^{1c}$ represents an n2-valent alkane, an n2-valent alkene, an n2-valent alkyne, an n2-valent arene, an n2-valent heterocyclic group, a trivalent phosphoric acid group, a phosphanetriyl group, an isocyanurate group, or an n2-valent group formed by combining two or more groups and bonds selected from the group consisting of the aforementioned groups, an alkylene group, an alkenylene group, an alkynylene group, an arylene group, —O—, —S—, —$NR^a$—, an ester bond, a thioester bond, an amide bond, a thioamide bond, and a sulfonyl group, $R^a$ represents a hydrogen atom or a substituent, $Y^4$, $Y^7$, $Y^{10}$, and $Y^{13}$ each represent a hydroxy group or an alkoxy group, $Y^5$, $Y^6$, $Y^8$, $Y^9$, $Y^{11}$, $Y^{12}$, $Y^{14}$, and $Y^{15}$ each represent a hydroxy group, an alkoxy group, an alkyl group, or a ketoxime group, and n2 is 3 or 4, provided that the compound represented by any of general formulae (2) to (4) includes none of a vinyl silane coupling agent, a (meth)acrylic silane coupling agent, an epoxy silane coupling agent, an amino silane coupling agent, and a sulfanyl silane coupling agent.

9. The flexible tube for an endoscope according to claim 1, wherein the aluminum alkoxide compound includes a compound represented by general formula (a) or (b) below,

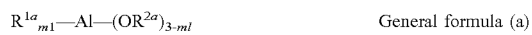

$R^{1a}{}_{m1}$—Al—$(OR^{2a})_{3-m1}$ General formula (a)

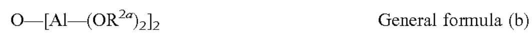

O—[Al—$(OR^{2a})_2]_2$ General formula (b)

where $R^{1a}$ represents a hydrogen atom, an alkyl group, a cycloalkyl group, an acyl group, an aryl group, or an unsaturated aliphatic group, $R^{2a}$ represents a hydrogen atom, an alkyl group, a cycloalkyl group, an acyl group, an alkenyl group, an aryl group, a phosphonate group, or —$SO_2R^{S1}$, where $R^{S1}$ represents a substituent, and m1 is an integer of 0 to 2.

10. The flexible tube for an endoscope according to claim 9, wherein in general formulae (a) and (b), at least one of $OR^{2a}$ has an acetonato structure or an acetato structure.

11. The flexible tube for an endoscope according to claim 1, wherein the zirconium alkoxide compound includes a compound represented by general formula (c) or (d) below,

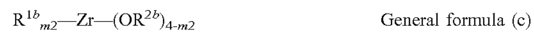

$R^{1b}{}_{m2}$—Zr—$(OR^{2b})_{4-m2}$ General formula (c)

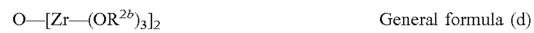

O—[Zr—$(OR^{2b})_3]_2$ General formula (d)

where $R^{1b}$ represents a hydrogen atom, an alkyl group, a cycloalkyl group, an acyl group, an aryl group, or an unsaturated aliphatic group, $R^{2b}$ represents a hydrogen atom, an alkyl group, a cycloalkyl group, an acyl group, an alkenyl group, an aryl group, a phosphonate group, or —$SO_2R^{S2}$, where $R^{S2}$ represents a substituent, and m2 is an integer of 0 to 3.

12. The flexible tube for an endoscope according to claim 11, wherein in general formulae (c) and (d), at least one of $OR^{2b}$ has an acetonato structure, an acetato structure, or a lactato structure.

13. The flexible tube for an endoscope according to claim 1, wherein the titanium alkoxide compound includes a compound represented by general formula (e) or (f),

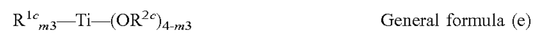

$R^{1c}{}_{m3}$—Ti—$(OR^{2c})_{4-m3}$ General formula (e)

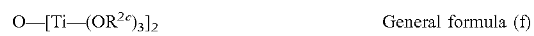

O—[Ti—$(OR^{2c})_3]_2$ General formula (f)

where $R^{1c}$ represents a hydrogen atom, an alkyl group, a cycloalkyl group, an acyl group, an aryl group, or an unsaturated aliphatic group, $R^{2c}$ represents a hydrogen atom, an alkyl group, a cycloalkyl group, an acyl group, an alkenyl group, an aryl group, a phosphonate group, or —$SO_2R^{S3}$, where $R^{S3}$ represents a substituent, and m3 is an integer of 0 to 3.

14. The flexible tube for an endoscope according to claim 13, wherein the compound represented by general formula (e) or (f) includes at least one atom selected from the group consisting of N, P, and S.

15. A method for producing a flexible tube for an endoscope, the method comprising:

a step of forming, on at least an outer periphery of a flexible-tube base containing metal as a constituent material, a primer layer including at least one of a silane coupling agent, an aluminum alkoxide compound, a zirconium alkoxide compound, or a titanium alkoxide compound; and a step of forming, on the primer layer formed on the outer periphery of the flexible-tube base, a cover layer using a cover layer-forming material that includes a polyester having a naphthalene structure, provided that the silane coupling agent includes none of a vinyl silane coupling agent, a (meth)acrylic silane coupling agent, an epoxy silane coupling agent, an amino silane coupling agent, and a sulfanyl silane coupling agent.

16. The method for producing a flexible tube for an endoscope according to claim 15, wherein the silane coupling agent excludes a compound represented by general formula (A) below:

General formula (A)

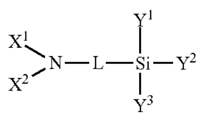

in the formula (A), $X^1$ and $X^2$ each represent a hydrogen atom, an alkyl group, a cycloalkyl group, an alkenyl group, an aryl group, an acyl group, an alkoxycarbonyl group, or a carbamoyl group, $Y^1$ represents a hydroxy group or an alkoxy group, $Y^2$ and $Y^3$ each represent a hydroxy group, an alkoxy group, or an alkyl group, L represents a single bond, or a divalent group selected from an alkylene group, an arylene group, and —O—, or a divalent group formed by combining two or more divalent groups thereof.

17. A method for producing an endoscopic medical device, the method comprising:

a step of obtaining a flexible tube for an endoscope by the method for producing a flexible tube for an endoscope according to claim 15; and a step of incorporating the obtained flexible tube for an endoscope into an insertion section of an endoscopic medical device.

18. A method for producing an endoscopic medical device, the method comprising:

incorporating the flexible tube for an endoscope according to claim 1 into an insertion section of an endoscopic medical device.

* * * * *